US007820706B2

(12) United States Patent
Casper et al.

(10) Patent No.: US 7,820,706 B2
(45) Date of Patent: *Oct. 26, 2010

(54) MULTIPLE DOSE AROMATASE INHIBITOR FOR TREATING INFERTILITY

(75) Inventors: Robert F. Casper, Toronto (CA); Mohamed F. M. Mitwally, North York (CA)

(73) Assignee: Ares Trading S.A., Aubonne (CH)

( * ) Notice: Subject to any disclaimer, the term of this patent is extended or adjusted under 35 U.S.C. 154(b) by 1707 days.

This patent is subject to a terminal disclaimer.

(21) Appl. No.: 10/475,175

(22) PCT Filed: Apr. 17, 2001

(86) PCT No.: PCT/CA01/00517

§ 371 (c)(1),
(2), (4) Date: May 25, 2004

(87) PCT Pub. No.: WO02/083146

PCT Pub. Date: Oct. 24, 2002

(65) Prior Publication Data

US 2004/0235804 A1 Nov. 25, 2004

(51) Int. Cl.
*A01N 43/64* (2006.01)
*A61K 31/41* (2006.01)
(52) U.S. Cl. .................................................. 514/383
(58) Field of Classification Search ................. 514/169, 514/177, 383
See application file for complete search history.

(56) References Cited

U.S. PATENT DOCUMENTS

| 4,845,227 A | * | 7/1989 | Hirsch et al. | 548/250 |
| 6,953,774 B2 | * | 10/2005 | Palmer et al. | 514/2 |
| 7,078,236 B2 | * | 7/2006 | Palmer et al. | 436/65 |

FOREIGN PATENT DOCUMENTS

| DE | 43 300 237 | 3/1995 |
| DE | 196 22 457 | 11/1997 |

OTHER PUBLICATIONS

Dowsett ("Aromatase Inhibitors come of age" Annals of Oncology, 8, 1997, 631-632).*
"The Ovulatory Cycle and Drug Therapy-Letrozole Protocol", Internet, 'Online!, Feb. 2001, Retrieved from the Internet: URL:http://www.babymakers.com/theovulatiorycycleand-drugtherapy.html, retrieved on Jul. 10, 2002.
Mohamed F. M. Mitwally et al, "Use of an Aromatase Inhibitor for Induction of Ovulation in Patients with an Inadequate Response to Clomiphene Citrate", Fertility and Sterility, vol. 75, No. 2, Feb. 2001, pp. 305-309.
Mohamed F. Mitwally et al, "Aromatase Inhibition: A Novel Method of Ovulation Induction in Women with Polycyctic Ovary Syndrome", Reproductive Technologies, vol. 10, No. 5, 2000, pp. 244-247.

Afonso et al., "Effects of the Aromatase Inhibitor Fadrozole on Plasma Sex Steroid Secretion and Ovulation Rate in Female Coho Salmon, Oncorhynchus kisutch, Close to Final Maturation", General and Comparative Endocrinology, 113:221-229 (1999).
Sioufi et al., Biopharm. & Drug Disposition, 189:779-789 (1997).
Mitwally et al., The Aromatase Inhibitor, Letrozole: a Promising Alternative for Clomiphene Citrate for Induction of Ovulation. [Abstract No. O-091] In: Program and abstracts of The 56th Annual Meeting of the American Society for Reproductive Medicine (ASRM), Oct. 2000, San Diego, CA, USA.
Mitwally et al., The Aromatase Inhibitor, Letrozole, Decreases FSH Dose Required for Ovarian Superovulation. CFAS meeting: Newfoundland, Canada, Sep. 2000.
Mitwally et al., Aromatase Inhibition Decreases FSH Dose Needed During Controlled Ovarian Hyperstimulation: A Controlled Prospective trial. Meeting of the Society for Gynecologic Investigation, Mar. 2001, Toronto, Canada. Abstract published in J. Soc. Gynecol. Invest. 8 2001; p. 85A.
Mitwally et al., Aromatase Inhibition Improves Ovarian Response to FSH: A Potential Option for Low Responders During Ovarian Stimulation. The 48th meeting of the Pacific Coast Fertility Society Meeting, Rancho Las Palmas Resort and Spa, CA, USA. Apr. 2001.
Mitwally et al., The Use of an Aromatase Inhibitor for Induction of Ovulation in Cases of Clomiphene Citrate Failure, Hum. Reprod., 15:71-72 (2000).
Mitwally et al., Aromatase Inhibition Improves Ovarian Response to Follicle Stimulating Hormone in Poor Responders, Fertil. Steril., 77:776-780 (2002).
Mitwally et al., Aromatase Inhibition for Ovarian Stimulation: Future Avenues for Infertility Management, Curr. Opin. Obster. Gynecol., 14:255-263 (2002).
Mitwally et al., Aromatase Inhibition Improves Response to Conrolled Ovarian Hyperstimulation without the Antiestrogenic Effects of Clomiphene Citrate, ESHRE meeting: Lausanne, Switzerland, Jul. 2001.

(Continued)

*Primary Examiner*—Yong S Chong
(74) *Attorney, Agent, or Firm*—Marshall, Gerstein & Borun LLP

(57) ABSTRACT

A method of inducing ovulation in a female suffering from anovulatory infertility which comprises administering to said female two or more daily doses of at least one aromatase inhibitor. A method for augmenting ovulation in an ovulating female suffering from unexplained infertility or another type of ovulatory infertility which comprises administering to said female two or more daily doses of at least one aromatase inhibitor early in one or more menstrual cycles. A method of substantially reducing dosage levels of follicle stimulating hormone (FSH) for administration to a female undergoing infertility treatment which comprises administering a combination of two or more daily doses of at least one aromatase inhibitor (AI) with a plurality of daily doses of follicle stimulating hormone (FSH). A method of increasing response to a follicle stimulating hormone from a female who is a poor responder to follicle stimulation, which comprises administering a combination of two or more daily doses or at least one aromatase inhibitor (AI) with a plurality of daily doses of follicle stimulating hormone (FSH). Also disclosed are related pharmaceutical preparations and uses.

22 Claims, 2 Drawing Sheets

OTHER PUBLICATIONS

Feutrie et al., Aromatase Inhibitors, Bull. Cancer, 86(10):821-827 (1999).

Coombes et al., Aromatase Inhibitors and Their Use in the Sequential Setting, Endocrine-Related Cancer, 6:259-263 (1999).

Dowsett et al., Anastrozole—A New Generation in Aromatase Inhibition: Clinical Pharmacology, Oncology, 54(Suppl 2):11-14 (1997).

Lipton et al., Letrozole: A Phase I Study of a New Potent Oral Aromatase Inhibitor of Breast Cancer, Cancer, 75(8):2132-2138 (1995).

Dowsett et al., Vorozole Results in Greater Oestrogen Suppression than Formestane in Postmenopausal Women and When Added to Goserelin in Premonopausal Women with Advanced Breast Cancer, Breast Cancer Research and Treatment, 56:25-34 (1999).

Dowsett, "Biological Background to Aromatase Inhibition," *The Breast*, vol. 5, pp. 196-201 (1996).

Feutrie, "Aromatase Inhibitors," *Bulletin du Cancer*, vol. 86, No. 10, pp. 821-827 (1990).

Marty et al., "ALS, a New Potent, Selective Aromatase Inhibitor Superior to Aminoglutethimide (AG) in Postmenopausal Women With Advanced Breast Cancer Previously Treated With Antioestrogens," *Proc Am Soc Clim Oncol*, vol. 16, pp. 156 (1997).

Mitwally et al., "Aromatase Inhibition Decreases FSH Dose Needed During Controlled Ovarian Hyperstimulation: A Controlled Prospective Trial," Meeting of the Society for Gynecologic Investigation, Abstract published in *J. Soc. Gynecol. Invest.*, vol. 8, pp. 85A (2001).

Mitwally et al., "Aromatase Inhibition Improves Ovarian Response to FSH: A Potential Option for Low Responders During Ovarian Stimulation," The 48th Meeting of the Pacific Coast Fertility Society Meeting, Rancho Las Palmas Resort and Spa, (2001).

Mitwally et al., "Aromatase Inhibition: A Novel Method of Ovulation Induction in Women With Polycystic Ovarian Syndrome," *Reprod Technol*, vol. 10, No. 5, pp. 244-247 (2001).

Mitwally et al., "The Aromatase Inhibitor, Letrozole: a Promising Alternative for Clomiphene Citrate for Induction of Ovulation, " Program and Abstracts of the 56th Annual Meeting of the American Society for Reproductive Medicine (ASRM), Oct. 2000, San Diego.

Mitwally et al., "The Use of an Aromatase Inhibitor for Induction of Ovulation in Cases of CLomiphene Citrate Failure," *Hum. Reprod.*, vol. 16, pp. 71-72 (2000).

The Ovulatory Cycle and Drug Therapy-Letrozole Protocol: Internet "Online Feb. 2001"; http://www.baby-makers.com/theovulatorycycleanddrugtherapy.html.

Adashi, "Clomiphene Citrate: Mechanism(s) and site(s) of Action—a Hypothesis Revisited," *Fertil Steril*, vol. 42, No. 3, pp. 331-344 (1984).

Akhtar et al., "Mechanistic Studies on Aromatase and Related C-C Bond Cleaving P-450 Enzymes," *J. Steroid Biochem Mol Biol*, vol. 44, pp. 375-387 (1993).

Archer et al., "Effects of Clomiphene Citrate on Episodic Luteinizing Hormone Secretion Throughout the Menstrual Cycle," *Am J. Obstet Gynecol*, vol. 161, No. 3, pp. 581-589 (1989).

Basir et al., "Morphometric Analysis of Peri-Implantation Endometrium in Patients Having Excessively High Oestradiol Concentrations After Ovarian Stimulation," *Hum. Reprod.*, vol. 16, No. 3, pp. 435-440 (2001).

Bateman et al., "Exogenous Estrogen Therapy for Treatment of Clomiphene Citrate—Induced Cervical Mucus Abnormalities: Is It Effective?" *Fertil Steril*, vol. 54, pp. 577-579 (1990).

Ben-Ami et al., "Exogenous Estrogen Therapy Concurrent with Clomiphene Citrate—Lack of Effect on Serum Sex Hormone Levels and Endometrial Thickness," *Gynecol Obstet Invest*, vol. 37, No. 3, pp. 180-182 (1994)/.

Cole et al., "Mechanism and Inhibition of Cytochrome P-450 Aromatase," *J. Med. Chem.*, vol. 33, pp. 2933-2944 (1990).

Coombes et al., "4-Hydroxyandrostenedione Treatment of Postmenopausal Patients with Advanced Breast Cancer," *The Lancet 2*, pp. 1237-1239 (1984).

Dickey et al., "Observations on the Mechanism of Action of Clomiphene (MRL-41)," *Fertil Steril*, vol. 16, pp. 485-494 (1965).

Fisch et al., "Unexplained Infertility: Evaluation of Treatment with Clomiphene Citrate and Human Chorionic Gonadotropin," *Fertil Steril*, vol. 51, pp. 828-833 (1989).

Fluker et al., "Exogenous Gonadotropin Therapy in World Health Organization Groups I and II Ovulatory Disorders," *Obstet Gynecol*, vol. 83, pp. 189-196 (1994).

Forman et al., "Evidence for an Adverse Effect of Elevated Serum Estradiol Concentration on Embryo Implantation," *Fertil Steril*, vol. 49, pp. 118-121 (1988).

Menopausal Gonadotropin/Human Chorionic Gonadotropin for In Vitro Fertilization, *Fertil Steril*, vol. 41, pp. 31-35 (1984).

Garcia et al., "The Use of Clomiphene Citrate," *Fertil Steril*, vol. 28, pp. 707-717 (1997).

Geisler et al., "Influence of Anastrozie (Arimidex), a Selective, Non-Steroidal Aromatase Inhibitor, on In Vitro Aromatisation and Plasma Oestrogen Levels in Postmenopausal Women with Breast Cancer," *Br J Cancer*, vol. 74, pp. 1286-1291 (1996).

Gelety et al., "The Effect of Clomiphene Citrate and Menopausal Gonadotropins on Cervical Mucus in Ovulatory Cycles," *Fertil Steril*, vol. 60, pp. 471-476 (1993).

Goldfarb et al., "Critical Review of 160 Clomiphene-related Pregnancies," *Obstet Gynecol*, vol. 31, pp. 342-345 (1968).

Gonen et al., "Determination of an Adverse Effect of Clomiphene Citrate on Endometrial Growth," *Hum Reprod*, vol. 5, pp. 670-674 (1990).

Graf et al., "Histologic Evaluation of the Luteal Phase in Women Following Follicle Aspiration for Oocyte Retrieval," *Fertil Steril*, vol. 49, pp. 616-619 (1988).

Hadi et al., "Ovulation Induction and Endometrial Steroid Receptors," *Hum. Reprod.*, vol. 9, pp. 2405-2410 (1994).

Kettel et al., "Hypothalamic-pituitary-ovarian Response to Clomiphene Citrate in Women with Polycystic Ovary Syndrome," *Fertil Steril*, vol. 59, No. 3, pp. 532-538 (1993).

Kolb et al., "Ultrastructural Characteristics of the Luteal Phase Endometrium in Patients Undergoing Controlled Ovarian Stimulation," *Fertil Steril*, vol. 67, pp. 625-630 (1997).

Macrow et al., "Endometrial Structure After Superovulation: A Prospective Controlled Study," *Fertil Steril*, vol. 61, pp. 696-699 (1994).

Mikkelson et al., "Single-dose Pharmacokinetics of Clomiphene Citrate in Normal Volunteers," *Fertil Steril*, vol. 46, pp. 392-396 (1986).

Mitwally et al., "Aromatase Inhibition for Ovarian Stimulation: Future Avenues for Infertility Management," *Currenty Opinion in Obstetrics & Gynecology*, vol. 14 (2002) (Abstract).

Mitwally et al., "Aromatase Inhibition Improves Ovarian Response to Follicle-Stimulating Hormone in Poor Responders," *Fertility & Sterility*, vol. 77, pp. 776-780 (2002) (Abstract).

Mitwally et al., "Use of an Aromatase Inhibitor for Induction of Ovulation in Patients with an Inadequate Response to Clomiphene Citrate," *Fertil Steril*, vol. 75, No. 2, pp. 305-309 (2001).

Nargund et al., "Cumulative Conception and Live Birth Rates in Natural (unstimulated) IVF Cycles," *Hum. Reprod.*, vol. 16, pp. 259-262 (2001).

Nebert et al., "The P-450 Superfamily: Update on New Sequences, Gene Mapping and Recommended Nomenclature," *DNA Mol. Biol.*, vol. 10, pp. 1-14 (1991).

Ng et al., "High Serum Oestradiol Concentration in Fresh IVF Cycles do not Impair Implantation and Pregnancy Rates in Subsequent Frozen-Thawed Embryo Transfer Cycles," *Hum. Reprod.*, vol. 15, pp. 250-255 (2000).

Noci et al., "Hormonal Patterns, Steroid Receptors and Morphological Pictures of Endometrium in Hyperstimulated IVF Cycles," *Eur. J. Obstet. Gynecol. Reprod. Biol.*, vol. 75, pp. 215-220 (1997).

Paulson et al., "Factors Affecting Embryo Implantation After Human In Vitro Fertilization: A Hypothesis," *Am J Obstet Gynecol*, vol. 163, pp. 2020-2023 (1990).

Randall et al., "Cervical Mucus Score and In Vitro Sperm Mucus Interaction in Spontaneous and Clomiphene Citrate Cycles," *Fertil Steril*, vol. 56, pp. 465-468 (1991).

Saleh et al., "Effects of Tamoxifen (Tx) on Endometrial Thickness and Pregnancy Rates in Women Undergoing Superovulation with Clomiphene Citrate (CC) and Intrauterine Insemination (IUI)," *Fertil Steril*, vol. 74, No. S1, pp. S90 (2000).

Santen et al., "Endocrine Treatment of Breast Cancer in Women," *Endocrine Rev*, vol. 11, pp. 1-45 (1990).

Santen et al., "Successful Medical Adrenalectomy with Aminoglutethimide: Role of Altered Drug Metabolism," *J. Am. Med. Assoc.*, vol. 230, pp. 1661 (1974).

Seif et al., "Endometrium in In-Vitro Fertilization Cycles: Morphological and Functional Differentiation in the Implantation Phase," *Hum. Reprod.*, vol. 7, pp. 6-11 (1992).

Sereepapong et al., "Effects of Clomiphene Citrate on the Endometrium of Regularly Cycling Women," *Fertil Steril*, vol. 73, pp. 287-291 (2000).

Shetty et al., "Effect of Estrogen Deprivation on the Reproductive Physiology of Male and Female Primates, " *J Steroid Biochem Biol*, vol. 61, pp. 157-166 (1997).

Simon et al., "Clinical Evidence for a Detrimental Effect on Uterine Receptivity of High Serum Oestradiol Concentrations in High and Normal Responder Patients," *Hum. Reprod.*, vol. 10, pp. 2432-2437 (1995).

Simon et al., "Increasing Uterine Receptivity by Decreasing Estradiol Levels During the Preimplantation Period in High Responders with the Use of a Follicle-Stimulating Hormone Step-Down Regimen," *Fertil Steril*, vol. 70, pp. 234-239 (1998).

Sinha et al., Effects of CGS20267 on Ovarian Aromatase and Gonadotropin Levels in the Rat, *Breast Cancer Res Treat*, vol. 48, pp. 45-51 (1998).

Sioufi et al., "Comparative Bioavailability of Letrozole Under Fed and Fasting Conditions in 12 Healthy Subjects After a 2.5 mg Single Oral Administration," *Biopharm Drug Dispos*, vol. 18, No. 6, pp. 779-797 (1997).

Sterzik et al., "In Vitro Fertilization: The Degree of Endometrial Insufficiency Varies with the Type of Ovarian Stimulation," *Fertil Steril*, vol. 50, pp. 457-462 (1988).

Taymor, "The Regulation of Follicle Growth: Some Clinical Implications in Reproductive Endocrinology," *Fertil Steril*, vol. 65, No. 2, pp. 235-247 (1996).

Tortoriello et al., "'Coasting' Does Not Adversely Affect Cycle Outcome in a Subset of Highly Responsive In Vitro Fertilization Patients," *Fertil Steril*, vol. 69, No. 3, pp. 454-460 (1998).

Trunet et al., "Open Dose-Finding Study of a New Potent and Selective Nonsteroidal Aromatase Inhibitor, CGS 20 267, in Healthy Male Subjects," *J Clinc Endocrinol Metab*, vol. 77, pp. 319-323 (1993).

Valbuena et al., "Increasing Levels of Estradiol are Deleterious to Embryonic Implantation Because They Directly Affect the Embryo," *Fertil Steril*, vol. 76, pp. 962-968 (2001).

Vendola et al., "Androgens Stimulate Early Stages of Follicular Growth in the Primate Ovary," *J Clin Invest*, vol. 101, No. 12, pp. 2622-2629 (1998).

Weil, et al., "Androgen and Follicle-Stimulating Hormone Interactions in Primate Ovarian Follicle Development," *J Clin Endocrinol Metab*, vol. 84, No. 8, pp. 2951-2956 (1999).

Wu et al., "The Effect of Therapy Initiation Day on Clomiphene Citrate Therapy," *Fertil Steril*, vol. 52, pp. 564-568 (1989).

Wysowski, "Use of Fertility Drugs in the United States, 1979 through 1991," *Fertil Steril*, vol. 60, pp. 1096-1098 (1993).

Yagel et al., "The Effect of Ethinyl Estradiol on Endometrial Thickness and Uterine Volume During Ovulation Induction by Clomiphene Citrate," *Fertil Steril*, vol. 57, pp. 33-36 (1992).

\* cited by examiner

MULTIPLE DOSE AROMATASE INHIBITOR FOR TREATING INFERTILITY

FIELD OF THE INVENTION

This invention relates to the use of multiple doses of aromatase inhibitors (AIs) for inducing and augmenting ovulation in females with anovulatory infertility or unexplained infertility and other types of ovulatory infertility. Also described is the use of AIs together with follicle stimulating hormone (FSH) for controlled ovarian hyperstimulation. Also disclosed are pharmaceutical formulations comprising the aromatase inhibitors and methods for administering them to females.

BACKGROUND OF THE INVENTION

In women with WHO type II anovulatory infertility such as polycystic ovary syndrome (PCOS), the treatment of first choice for the induction of ovulation is an anti-estrogen. The most commonly used drug is clomiphene citrate (CC). However, 20 to 25 percent of women do not ovulate with CC. In addition, clinical data reveal a discrepancy between ovulation and conception rates during CC treatment[1], and a higher than expected incidence of miscarriage in conception cycles[2]. These observations have been attributed to the anti-estrogenic mechanism of action of CC resulting in long-lasting estrogen receptor depletion. Thus, CC may have a negative effect on the quality and quantity of cervical mucus[3], on endometrial development[4], and on other as yet undetermined fertility factors since CC is accumulated in the body as a result of its long half-life[5].

In CC failures, gonadotropin preparations such as human menopausal gonadotropin (hMG) or follicle stimulating hormone (FSH) have been used as a second-line treatment for ovulation induction. In women with polycystic ovary syndrome, because of the high sensitivity of the ovaries to gonadotropin stimulation, treatment with hMG or FSH is difficult to control and characteristically induces multiple follicles. The result is a high frequency of multiple pregnancies and increased risk of ovarian hyperstimulation syndrome (OHSS)[6]. Therefore, a simple oral treatment that could be used without risk of hyperstimulation and with minimal monitoring is the preferred first line of therapy.

Additionally, although it has been established that pregnancy rates for women who take CC are less than expected based on ovulation rates, CC therapy is widely administered to women with unexplained infertility, often without ultrasound monitoring, in order to induce the development of multiple follicles[7]. The use of CC in these women may be unsuccessful because of antiestrogenic effects on endometrial development. A recent study has prospectively applied morphometric analysis of the endometrium, which is a quantitative and objective technique to study the effect of CC on the endometrium in a group of normal women. In this study, CC was found to have a deleterious effect on the endometrium, demonstrated by a reduction in glandular density and an increase in the number of vacuolated cells[8]. In some exceptional cases, normal ovulatory women may receive 6 to 12 cycles of CC before it is finally determined that the anti-estrogenic effects of CC on the endometrium are actually causing an anti-conception action. For these reasons, a simple, inexpensive and safe alternative to CC for use in normally ovulatory women, in whom frequent cycle monitoring is difficult, is also required.

The induction of ovulation constitutes a vital part of infertility management. Unfortunately, most current therapeutic approaches for induction of ovulation have been empiric[9]. For over 40 years, clomiphene citrate (CC) has been the most commonly used treatment for the induction and augmentation of ovulation, accounting for about two thirds of the fertility drugs prescribed in the United States[10]. However, the mechanism(s) and site(s) of CC action have only been partially clarified despite extensive clinical research[11].

Mechanism of CC Action

It is believed that the 2 isomers of CC exert either an anti-estrogenic effect (zu-clomiphene) or a weak estrogen agonist effect (en-clomiphene) at estrogen binding sites in the pituitary and hypothalamus, thus releasing the hypothalamic/pituitary axis from the inhibitory effect of the major circulating estrogen, estradiol $(E_2)$[12]. In women with PCOS, CC-induced ovulation was accompanied by increased secretion of LH and FSH with enhanced estrogen secretion. Increased LH pulse amplitude after CC, together with decreased pituitary sensitivity to a GnRH bolus, suggested that CC acted predominantly on the hypothalamus to cause release of larger pulses of GnRH into the pituitary-portal system[13]. Similar findings have been reported in normal ovulatory women[14]. Various mechanisms of CC action have also been suggested at the level of the pituitary and/or the ovary. In particular, the ovarian actions of CC have not been widely appreciated[15]. However, the overall mechanism of CC action may be the sum of its effects on the hypothalamus, pituitary and ovary as discussed by Adashi[16].

Approaches to Improve Pregnancy Outcome with CC

In order to improve the outcome of CC treatment, various approaches have been suggested to overcome the antiestrogenic effect of CC. One approach has been to administer estrogen concomitantly during CC treatment to attain high estrogen levels to overcome the antiestrogenic effect of CC. Some investigators have reported success with this approach[17] while others have reported no benefit[18] or even a deleterious effect of estrogen administrations[19]. Another approach to reduce adverse effects has been to administer CC earlier during the menstrual cycle rather than starting on day 5[20], in the hopes of allowing the anti-estrogenic effect to wear off to some extent. A third approach has been to combine another selective estrogen receptor modulator like tamoxifen, which has more estrogen agonistic effect on the endometrium with CC[21]. However, none of the above mentioned strategies has proved to be completely successful in avoiding the peripheral antiestrogenic effects of CC. In addition to a discrepancy between ovulation and pregnancy rates with CC treatment, 20% to 25% of anovulatory women are resistant to CC and fail to ovulate at doses up to 150 mg daily. In CC failures, gonadotropins have been used as a second-line treatment for ovulation induction. However, they are associated with higher risk of multiple pregnancy, and severe ovarian hyperstimulation syndrome, especially in women with PCOS. Therefore, a simple oral alternative to CC that could be used without high risk and which requires minimal monitoring would be the preferred first line of therapy for ovulation induction.

Aromatase Inhibitor

A group of highly selective AIs has been approved for use in postmenopausal women with breast cancer to suppress estrogen production. These AIs have a relatively short half-life (approximately 48 hours) compared to CC, and therefore would be eliminated from the body rapidly[22]. In addition, since no estrogen receptor down-regulation occurs, no adverse effects on estrogen target tissues, as observed in CC treated cycles, would be expected.

Physiology of Aromatase Enzyme

Aromatase is a cytochrome P-450 hemoprotein-containing enzyme complex that catalyzes the rate-limiting step in the production of estrogens, i.e. the conversion of androstenedione and testosterone, via three hydroxylation steps, to estrone and estradiol[23]. Aromatase activity is present in many tissues, such as the ovaries, adipose tissue, muscle, liver, breast tissue, and in malignant breast tumors. The main sources of circulating estrogens are the ovaries in premenopausal women and adipose tissue in post-menopausal women[24]. Although aromatase has features in common with other steroidogenic P450 enzymes, the heme-binding region has only 17.9±93.5% amino acids identical to those of other steroidogenic P-450 enzymes. This observation suggests that P-450arom belongs to a separate gene family which has been designated CYP19[25]. Aromatase catalyzes the conversion of androgens to estrone ($E_1$), which is further converted to the potent estrogen estradiol ($E_2$) by the enzyme 17β-HSD type 1 in the granulosa cell.

Development of Aromatase Inhibitors

Aromatase is a good target for selective inhibition because estrogen production is a terminal step in the biosynthetic sequence. There are two types of aromatase inhibitors; steroidal (type I inhibitors) and non-steroidal inhibitors (type II inhibitors). Type I steroidal aromatase inhibitors are all derivatives of androstenedione that act as a false substrate and bind irreversibly to the androgen-binding site with continuing treatment. For this reason, they are also called suicide inhibitors. 4-hydroxyandrostenedione, the first selective steroidal aromatase inhibitor to be used clinically, has proved to be effective in tamoxifen-resistant breast cancer patients and is available in many countries world-wide[26]. Type II non-steroidal aromatase inhibitors exert their function through binding to the heme moiety of the cytochrome P450 enzyme. The first of these inhibitors to be used clinically was aminoglutethimide, which induces a medical adrenalectomy by inhibiting many other enzymes involved in steroid biosynthesis[27]. Although aminoglutethimide is an effective hormonal agent in postmenopausal breast cancer, its use is complicated by the need for concurrent corticosteroid replacement, in addition to side effects like lethargy, rashes, nausea and fever that results in 8-15% of patients stopping treatment. The lack of specificity and unfavorable toxicity profile of aminoglutethimide have led to the search for more specific aromatase inhibitors. In addition, the above mentioned aromatase inhibitors were not able to completely inhibit aromatase activity in premenopausal patients[28].

Aromatase inhibitors such as anastrozole, ZN 1033, (Arimidex®), letrozole, CGS 20267. (Femara™) and vorozole (Rivizor®) are selective AIs, available for clinical use in North America and other parts of the world for treatment of postmenopausal breast cancer. These triazole (antifungal) derivatives are reversible, competitive AIs, which are highly potent and selective[29]. Their intrinsic potency is considerably greater than that of aminoglutethimide, and at doses of 1-5 mg/day, inhibit estrogen levels by 97% to >99%. This level of aromatase inhibition results in estradiol concentrations below detection by most sensitive immunoassays. The high affinity of AIs for aromatase is thought to reside in the N-4 nitrogen of the triazole ring that coordinates with the heme iron atom of the aromatase enzyme complex. AIs are completely absorbed after oral administration with mean terminal $t_{1/2}$ of approximately 50 hr (range, 30-60 hr). They are cleared from the systemic circulation mainly by the liver. Another AI available commercially is xemestane(Aromasin™) which is an example of a steroidal inhibitor with short half-life.

In animal studies, letrozole resulted in increased FSH and LH when given to mature female rats and about a 30% increase in ovarian weight[30]. In the bonnet monkey, treatment with aromatase inhibitors to induce estradiol deficiency led to development of multiple normal Graafian follicles in vivo, and normal response of granulosa and theca cells to gonadotropins in vitro (109)[31]. In vivo data describe a continuum of inhibition of aromatase, with aminoglutethimide (90%), vorozole (93%), anastrozole (97%), and letrozole (98.5%) displaying increasing potency and specificity[32]. Letrozole has an $IC_{50}$ of 11.5 nM in vitro and $ED_{50}$ of 1-3 μg/kg in vivo when given orally. The disposition of orally administered letrozole in healthy postmenopausal women is characterized by steady-state plasma concentrations in 4 to 8 hours, and a half-life of approximately 45 hours. The absolute systemic bioavailability of letrozole after oral administration was 100% compared with the same dose given intravenously[33]. Doses up to 30 mg have been well tolerated[34]. The lethal dose in mice and rats is approximately 2000 mg/kg. There is no experience in humans with an overdose of letrozole[35].

The following publications by the inventors disclose the subject matter of the present application.

The success of aromatase inhibition by letrozole in inducing ovulation in women with PCOS has been reported[36]. In a series of 10 patients with PCOS who either failed to ovulate (n=4) or ovulated with an endometrial thickness ≦5 mm (n=6) in response to CC administration, ovulation occurred in 7 of the 10 letrozole treated cycles (70%), with clinical pregnancy in 2 patients and chemical pregnancy in one patient. The mean number of mature follicles was 2.6, ranging from 1 to 4 follicles in the 7 ovulatory cycles. The mean level of estradiol on the day of hCG administration was 1076 pmol/L with mean estradiol per follicle of 378 pmol/L. This estradiol level allowed the growth of the endometrium to an adequate thickness that ranged from 0.7 cm to 0.9 cm on the day of hCG administration, showing the absence of antiestrogenic effects as seen with CC.

In a second study, comparable success of letrozole in inducing ovulation in 12 women with PCOS women, in addition to success in augmenting ovulation in a group of 10 ovulatory women was presented. Patients in both groups tried CC in prior treatment cycles with an inadequate response. With letrozole treatment, ovulation occurred in 9 of 12 cycles (75%) and pregnancy was achieved in 3 patients (25%) in the PCOS group. In the ovulatory group, letrozole resulted in a mean number of 2.3 mature follicles and a mean endometrial thickness of 0.8 cm. Pregnancy was achieved in one patient (10%)[37].

The use of letrozole in conjunction with FSH has been studied for controlled ovarian super ovulation in both ovulatory women with unexplained infertility and anovulatory women with PCOS[38]. The use of letrozole was associated with a significantly lower FSH dose required for achievement of adequate ovarian super ovulation. The pregnancy rate and endometrial thickness with letrozole and FSH treatment was similar to FSH alone. We have also shown an improvement in ovarian response to FSH stimulation with the use of letrozole in low responders during ovarian stimulation[39].

In U.S. Pat. No. 5,583,128 granted Dec. 10, 1996 to Bhatnagar, there is described the use of aromatase inhibitors for contraception in female primates of reproductive age without substantially affecting the menstrual cycle of the female primate. The contraceptive action of the aromatase inhibitors is reversible, that is to say once their use has been discontinued pregnancy can occur in the treated primates as early as the next cycle.

In U.S. Pat. No. 5,491,136 granted Feb. 13, 1996 to Peet et al, the use of aromatase inhibitors in the treatment of breast cancer is described.

All references referred to here are incorporated by reference into this application.

SUMMARY OF THE INVENTION

The present invention mimics the action of CC, without depletion of estrogen receptors, by administration of an aromatase inhibitor (AI) in the early part of the menstrual cycle. This is believed to result in release of the hypothalamic/pituitary axis from estrogenic negative feedback, thereby increasing gonadotropin secretion and resulting in stimulation of ovarian follicles. In addition, a peripheral mechanism of action at the level of the ovary may also be present, secondary to prevention of androgen conversion to estrogen and an increase in intra-ovarian androgen concentration. In the primate ovary, androgen has been shown to increase granulosa cell FSH receptors[40,41] (refs) thereby increasing ovarian responsiveness to FSH. The AIs preferred have a substantially shorter half life which means the AI does not accumulate in the body thereby providing therapy with decreased side effects as compared with CC.

In a first aspect the present invention provides a method of inducing ovulation in a female suffering from anovulatory infertility which comprises administering to said female two or more of daily doses of at least one aromatase inhibitor. Preferably, a total of 2 to 10 daily doses of the aromatase inhibitor are administered. Most preferably, a total of 5 daily doses of the aromatase inhibitor are administered.

Next, the invention provides a method for augmenting ovulation in an ovulating female suffering from unexplained infertility or another type of ovulatory infertility which comprises administering to said female two or more daily doses of at least one aromatase inhibitor early in one or more menstrual cycles.

In another aspect the invention provides a method of substantially reducing dosage levels of follicle stimulating hormone (FSH) for administration to a female which comprises administering a combination of two or more daily doses of at least one aromatase inhibitor (AI) with a plurality of daily doses of follicle stimulating hormone (FSH).

In some commercial forms of FSH, luteinizing hormone (LH) may also be present, and hence, the invention also encompasses daily doses of FSH and LH in place of daily doses of FSH alone.

The invention further provides a method of increasing response to follicle stimulating hormone in a female who is a poor responder to follicle stimulation, which comprises administering a combination of two or more daily doses of at least one aromatase inhibitor (AI) with daily doses of follicle stimulating hormone (FSH).

Another aspect provides a pharmaceutical preparation for treating infertility in a female comprising two or more daily doses of a composition comprising an effective amount for inducing or augmenting ovulation of an aromatase inhibitor together with a pharmaceutically acceptable carrier.

The invention also provides a two component pharmaceutical preparation for treating infertility in a female comprising two or more daily doses of an aromatase inhibitor together with a pharmaceutically acceptable carrier in combination with a plurality of daily doses of follicle stimulating hormone together with a pharmaceutically acceptable carrier. The infertility may arise in an anovulatory female or an ovulatory female suffering from unexplained infertility or other types of ovulatory infertility. Alternatively, the female may be a poor responder to follicle stimulation. Finally, the amount of FSH used in combination with AI is substantially less than in preparations where FSH is used alone.

The invention also provides for the use of two or more daily doses of an aromatase inhibitor for treating infertility in a female, each dose comprising an effective amount of an aromatase inhibitor for inducing or augmenting ovulation.

The invention also provides for the use of two or more daily doses of an aromatase inhibitor in combination with a plurality of daily doses of follicle stimulating hormone for treating infertility in a female wherein the amount of follicle stimulating hormone is substantially reduced as compared with the use of follicle stimulating hormone on its own.

The invention further provides for the use of two or more daily doses of an aromatase inhibitor in combination with a plurality of daily doses of follicle stimulating hormone for treating a female who is a poor responder to follicle stimulation to increase follicle production.

Another part of the invention comprises the use of two or more daily doses of an aromatase inhibitor in the preparation of a medicament for the treatment of infertility in a female.

Finally the invention provides for the use of two or more daily doses of an aromatase inhibitor in combination with a plurality of daily doses of follicle stimulating hormone for treating infertility in a female. The infertility problems are those described earlier.

DETAILED DESCRIPTION OF THE INVENTION

The female is preferably a human being, but use of the treatments to other species as appropriate is envisaged.

While one aromatase inhibitor is preferred for use in the present invention, combinations of aromatase inhibitors may be used especially those of aromatase inhibitors having different half-lives. The aromatase inhibitor is preferably selected from aromatase inhibitors having a half-life of about 8 hours to about 4 days, more preferably from aromatase inhibitors having a half-life of about 2 days. Most beneficial are those aromatase inhibitors selected from non-steroidal and reversible aromatase inhibitors. More detail on the types of aromatase inhibitors that may be used in the methods, uses and preparations of the present invention appears subsequently herein.

Aromatase Inhibitor

The aromatase inhibitors that have been found to be most useful of the commercially available forms are those in oral form. This form offers clear advantages over other forms, including convenience and patient compliance. Preferred aromatase inhibitors of those that are commercially available include anastrozole, letrozole, vorozole and exemestane. Exemestane (Aromasin™) is an example of a steroidal aromatase inhibitor that may be used in the present invention.

By "aromatase inhibitors" there are to be understood substances that inhibit the enzyme aromatase (=oestrogen synthetase), which is responsible for converting androgens to oestrogens.

Aromatase inhibitors may have a non-steroidal or a steroidal chemical structure. According to the present invention, both non-steroidal aromatase inhibitors and steroidal aromatase inhibitors can be used.

By aromatase inhibitors there are to be understood especially those substances that in a determination of the in vitro inhibition of aromatase activity exhibit $IC_{50}$ values of $10^{-5}$ M or lower, especially $10^{-6}$ M or lower, preferably $10^{-7}$ M or lower and most especially $10^{-8}$ M or lower.

The in vitro inhibition of aromatase activity can be demonstrated, for example, using the methods described in J. Biol. Chem. 249, 5364 (1974) or in J. Enzyme Inhib. 4, 169 (1990). In addition, $IC_{50}$ values for aromatase inhibition can be obtained, for example, in vitro by a direct product isolation method relating to inhibition of the conversion of 4-$^{14}$C-androstenedione to 4-$^{14}$C-oestrone in human placental microsomes.

By aromatase inhibitors there are to be understood most especially substances for which the minimum effective dose in the case of in vivo aromatase inhibition is 10 mg/kg or less, especially 1 mg/kg or less, preferably 0.1 mg/kg or less and most especially 0.01 mg/kg or less.

In vivo aromatase inhibition can be determined, for example, by the following method [see J. Enzyme Inhib. 4, 179 (1990)]: androstenedione (30 mg/kg subcutaneously) is administered on its own or together with a compound of the invention (orally or subcutaneously) to sexually immature female rats for a period of 4 days. After the fourth administration, the rats are sacrificed and the uteri are isolated and weighed. The aromatase inhibition is determined by the extent to which the hypertrophy of the uterus induced by the administration of androstenedione alone is suppressed or reduced by the simultaneous administration of the compound according to the invention.

The following groups of compounds are listed as examples of aromatase inhibitors. Each individual group forms a group of aromatase inhibitors that can be used successfully in accordance with the present invention:

(a) The compounds of formulae I and I* as defined in EP-A-165 904. These are especially the compounds of formula I

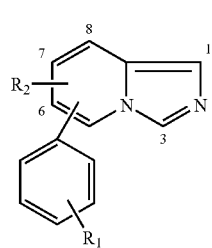

(I)

wherein $R_1$ is hydrogen, lower alkyl; lower alkyl substituted by hydroxy, lower alkoxy, lower alkanoyloxy, lower alkanoyl, amino, lower alkylamino, di-lower alkylamino, halogen, sulfo, carboxy, lower alkoxycarbonyl, carbamoyl or by cyano; nitro, halogen, hydroxy, lower alkoxy, lower alkanoyloxy, phenylsulfonyloxy, lower alkylsulfonyloxy, mercapto, lower alkylthio, lower alkylsulfinyl, lower alkylsulfonyl, lower alkanoylthio, amino, lower alkylamino, di-lower alkylamino, lower alkyleneamino, N-morpholino, N-thiomorpholino, N-piperazino that is unsubstituted or lower alkyl-substituted in the 4-position, tri-lower alkylammonio, sulfo, lower alkoxysulfonyl, sulfamoyl, lower alkylsulfamoyl, di-lower alkylsulfamoyl, formyl; iminomethyl that is unsubstituted or substituted at the nitrogen atom by hydroxy, lower alkoxy, lower alkanoyloxy, lower alkyl, phenyl or by amino; $C_2$-$C_7$ alkanoyl, benzoyl, carboxy, lower alkoxycarbonyl, carbamoyl, lower alkylcarbamoyl, di-lower alkylcarbamoyl, cyano, 5-tetrazolyl, unsubstituted or lower alkyl-substituted 4,5-dihydro-2-oxazolyl or hydroxycarbamoyl; and $R_2$ is hydrogen, lower alkyl, phenyl-lower alkyl, carboxy-lower alkyl, lower alkoxycarbonyl-lower alkyl, halogen, hydroxy, lower alkoxy, lower alkanoyloxy, mercapto, lower alkylthio, phenyl-lower alkylthio, phenylthio, lower alkanoylthio, carboxy, lower alkoxycarbonyl or lower alkanoyl; the 7,8-dihydro derivatives thereof; and the compounds of formula I*

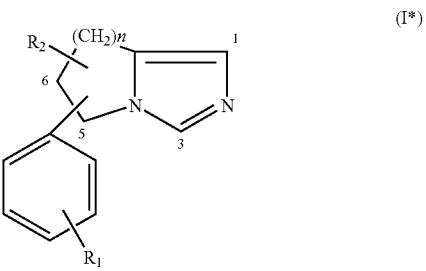

(I*)

wherein n is 0, 1, 2, 3 or 4; and $R_1$ and $R_2$ are as defined above for formula I; it being possible for the phenyl ring in the radicals phenylsulfonyloxy, phenyliminomethyl, benzoyl, phenyl-lower alkyl, phenyl-lower alkylthio and phenylthio to be unsubstituted or substituted by lower alkyl, lower alkoxy or by halogen; it being possible in a compound of formula I* for the two substituents $C_6H_4$—$R_1$ and $R_2$ to be linked to each of the saturated carbon atoms of the saturated ring, either both to the same carbon atom or both to different carbon atoms, and pharmaceutically acceptable salts thereof.

Individual compounds that may be given special mention here are:

(1) 5-(p-cyanophenyl)imidazo[1,5-a]pyridine,
(2) 5-(p-ethoxycarbonylphenyl)imidazo[1,5-a]pyridine,
(3) 5-(p-carboxyphenyl)imidazo[1,5-a]pyridine,
(4) 5-(p-tert-butylaminocarbonylphenyl)imidazo[1,5-a]pyridine,
(5) 5-(p-ethoxycarbonylphenyl)5,6,7,8-tetrahydroimidazo[1,5-a]pyridine,
(6) 5-(p-carboxyphenyl)-5,6,7,8-tetrahydroimidazo[1,5-a]pyridine,
(7) 5-(p-carbamoylphenyl)-5,6,7,8-tetrahydroimidazo[1,5-a]pyridine,
(8) 5-(p-tolyl)-5,6,7,8-tetrahydroimidazo[1,5-a]pyridine,
(9) 5-(p-hydroxymethylphenyl)imidazo[1,5-a]pyridine,
(10) 5-(p-cyanophenyl)-7,8-dihydroimidazo[1,5-a]pyridine,
(11) 5-(p-bromophenyl)-5,6,7,8-tetrahydroimidazo[1,5-a]pyridine,
(12) 5-(p-hydroxymethylphenyl)-5,6,7,8-tetrahydroimidazof[1,5-a]pyridine,
(13) 5-(p-formylphenyl)-5,6,7,8-tetrahydroimidazo[1,5-a]pyridine,
(14) 5-(p-cyanophenyl)-5-methylthio-5,6,7,8-tetrahydroimidazo[1,5-a]pyridine,
(15) 5-(p-cyanophenyl)-5-ethoxycarbonyl-5,6,7,8-tetrahydroimidazo[1,5-a]pyridine,
(16) 5-(p-aminophenyl)-5,6,7,8-tetrahydroimidazo[1,5-a]pyridine,
(17) 5-(p-formylphenyl)imidazo[1,5-a]pyridine,
(18) 5-(p-carbamoylphenyl)imidazo[1,5-a]pyridine,
(19) 5H-5-(4-tert-butylaminocarbonylphenyl)-6,7-dihydropyrrolo[1,2-c]imidazole,
(20) 5H-5-(4-cyanophenyl)-6,7-dihydropyrrolo[1,2-c]imidazole,
(21) 5H-5-(4-cyanophenyl)-6,7,8,9-tetrahydroimidazo[1,5-a]azepine,

(22) 5-(4-cyanophenyl)-6-ethoxycarbonylmethyl-5,6,7,8-tetrahydroimidazo[1,5-a]pyridine,
(23) 5-(4-cyanophenyl)-6-carboxymethyl-5,6,7,8-tetrahydroimidazo[1,5-a]pyridine
(24) 5-benzyl-5-(4-cyanophenyl)-5,6,7,8-tetrahydroimidazo[1,5-a]pyridine,
(25) 7-(p-cyanophenyl)-5,6,7,8-tetrahydroimidazo[1,5-a]pyridine,
(26) 7-(p-carbamoylphenyl)-5,6,7,8-tetrahydroimidazo[1,5-a]pyridine,
(27) 5-(p-cyanophenyl)-5,6,7,8-tetrahydroimidazo[1,5-a]pyridine (=Fadrozol).

(b) The compounds of formula I as defined in EP-A 236 940. These are especially the compounds of formula I

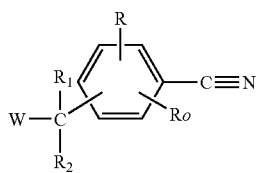

(I)

wherein R and $R_0$, independently of one another, are each hydrogen or lower alkyl, or R and $R_0$ at adjacent carbon atoms, together with the benzene ting to which they are bonded, form a naphthalene or tetrahydronaphthalene ring; wherein $R_1$ is hydrogen, lower alkyl, aryl, aryl-lower alkyl or lower alkenyl; $R_2$ is hydrogen, lower alkyl, aryl, aryl-lower alkyl, (lower alkyl, aryl or aryl-lower alkyl)-thio or lower alkenyl, or wherein $R_1$ and $R_2$ together are lower alkylidene or $C_4$-$C_6$ alkylene; wherein W is 1-imidazolyl, 1-(1,2,4 or 1,3,4)-triazolyl, 3-pyridyl or one of the mentioned heterocyclic radicals substituted by lower alkyl; and aryl within the context of the above definitions has the following meanings: phenyl that is unsubstituted or substituted by one or two substituents from the group lower alkyl, lower alkoxy, hydroxy, lower alkanoyloxy, nitro, amino, halogen, trifluoromethyl, cyano, carboxy, lower alkoxycarbonyl, carbamoyl, N-lower alkylcarbamoyl, N,N-di-lower alkylcarbamoyl, lower alkanoyl, benzoyl, lower alkylsulfonyl, sulfamoyl, N-lower alkylsulfamoyl and N,N-di-lower alkylsulfamoyl; also thienyl, indolyl, pyridyl or furyl, or one of the four last-mentioned heterocyclic radicals monosubstituted by lower alkyl, lower alkoxy, cyano or by halogen; and pharmaceutically acceptable salts thereof.

Individual compounds from that group that may be given special mention are:
(1) 4-[alpha-(4-cyanophenyl)-1-imidazolylmethyl]-benzonitrile,
(2) 4-[alpha-(3-pyridyl)-1-imidazolylmethyl]-benzonitrile,
(3) 4-[alpha-(4-cyanobenzyl)-1-imidazolylmethyl]-benzonitrile,
(4) 1-(4-cyanophenyl)-1-(1-imidazolyl)-ethylene,
(5) 4-[alpha-(4-cyanophenyl)-1-(1,4-triazolyl)methyl]-benzonitrile,
(6) 4-[alpha-(4-cyanophenyl)-3-pyridylmethyl]-benzonitrile.

(c) The compounds of formula I as defined in EP-A-408 509. These are especially the compounds of formula I

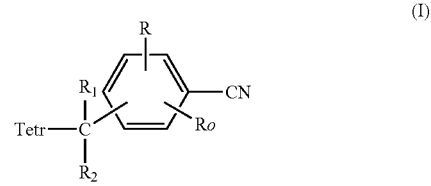

(I)

wherein Tetr is 1- or 2-tetrazolyl that is unsubstituted or substituted in the 5-position by lower alkyl, phenyl-lower alkyl or by lower alkanoyl; R and $R_2$, independently of one another, are each hydrogen; lower alkyl that is unsubstituted or substituted by hydroxy, lower alkoxy, halogen, carboxy, lower alkoxycarbonyl, (amino, lower alkylamino or di-lower alkylamino)-carbonyl or by cyano; lower alkenyl, aryl, heteroaryl, aryl-lower alkyl, $C_3$-$C_6$ cycloalkyl, $C_3$-$C_6$ cycloalkyl-lower alkyl, lower alkylthio, arylthio or aryl-lower alkylthio; or $R_1$ and $R_2$ together are straight-chained $C_4$-$C_6$ alkylene that is unsubstituted or substituted by lower alkyl, or are a group —$(CH_2)_m$-1,2-phenylene-$(CH_2)_n$— wherein m and n, independently of one another, are each 1 or 2 and 1,2-phenylene is unsubstituted or substituted in the same way as phenyl in the definition of aryl below, or are lower alkylidene that is unsubstituted or mono- or di-substituted by aryl; and R and $R_0$, independently of one another, are each hydrogen or lower alkyl; or R and $R_0$ together, located at adjacent carbon atoms of the benzene ring, are a benzo group that is unsubstituted or substituted in the same way as phenyl in the definition of aryl below; aryl in the above definitions being phenyl that is unsubstituted or substituted by one or more substituents from the group consisting of lower alkyl, lower alkoxy, hydroxy, lower alkanoyloxy, nitro, amino, halogen, trifluoromethyl, carboxy, lower alkoxycarbonyl, (amino, lower alkylamino or di-lower alkylamino)-carbonyl, cyano, lower alkanoyl, benzoyl, lower alkylsulfonyl and (amino, lower alkylamino or di-lower alkylamino)-sulfonyl; heteroaryl in the above definitions being an aromatic heterocyclic radical from the group consisting of pyrrolyl, pyrazolyl, imidazolyl, triazolyl, tetrazolyl, furanyl, thienyl, isoxazolyl, oxazolyl, oxadiazolyl, isothiazolyl, thiazolyl, thiadiazolyl, pyridyl, pyridazinyl, pyrimidyl, pyrazinyl, triazinyl, indolyl, isoindolyl, benzimidazolyl, benzotriazolyl, benzofuranyl, benzothienyl, benzoxazolyl, benzothiazolyl, benzoxadiazolyl, benzothiadiazolyl, quinolyl and isoquinolyl that is unsubstituted or substituted in the same way as phenyl in the definition of aryl above; and pharmaceutically acceptable salts thereof.

Individual compounds from that group that may be given special mention are:
(1) 4-(2-tetrazolyl)methyl-benzonitrile,
(2) 4-[α-(4-cyanophenyl )-(2-tetrazolyl)methyl]-benzonitrile,
(3) 1-cyano-4-(1-tetrazolyl)methyl-naphthalene,
(4) 4-[α-(4-cyanophenyl)-(1-tetrazolyl)methyl]-benzonitrile.

(d) The compounds of formula I as defined in European Patent Application No. 91810110.6. These are especially the compounds of formula I

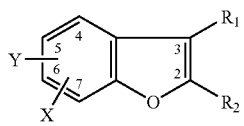

wherein X is halogen, cyano, carbamoyl, N-lower alkylcarbamoyl, N-cycloalkyl-lower alkylcarbamoyl, N,N-di-lower alkylcarbamoyl, N-arylcarbamoyl, hydroxy, lower alkoxy, aryl-lower alkoxy or aryloxy, wherein aryl is phenyl or naphthyl, each of which is unsubstituted or substituted by lower alkyl, hydroxy, lower alkoxy, halogen and/or by trifluoromethyl, Y is a group —$CH_2$-A wherein A is 1-imidazolyl, 1-(1,2,4-triazolyl), 1-(1,3,4-triazolyl), 1-(1,2,3-triazolyl), 1-(1,2,5-triazolyl), 1-tetrazolyl or 2-tetrazolyl, or Y is hydrogen, $R_1$ and $R_1$, independently of one another, are each hydrogen, lower alkyl or a group —$CH_2$-A as defined for Y, or $R_1$ and $R_2$ together are —$(CH_2)_n$— wherein n is 3, 4 or 5, with the proviso that one of the radicals Y, $R_1$ and $R_2$ is a group —$CH_2$-A, with the further proviso that in a group —$CH_2$-A as a meaning of $R_1$ or $R_2$, A is other than 1-imidazolyl when X is bromine, cyano or carbamoyl, and with the proviso that in a group —$CH_2$-A as a meaning of Y, A is other than 1-imidazolyl when X is halogen or lower alkoxy, $R_1$ is hydrogen and $R_2$ is hydrogen or lower alkyl, and pharmaceutically acceptable salts thereof.

Individual compounds from that group that may be given special mention are:
(1) 7-cyano-4-[1-(1,2,4-triazolyl)methyl]-2,3-dimethylbenzofuran,
(2) 7-cyano-4-(1-imidazolylmethyl)-2,3-dimethylbenzofuran,
(3) 7-carbamoyl-4-(1-imidazolylmethyl)-2,3-dimethylbenzofuran,
(4) 7-N-(cyclohexylmethyl)carbamoyl-4-(1-imidazolylmethyl)-2,3-dimethylbenzofuran.

(e) The compounds of formula I as defined in Swiss Patent Application 1339/90-7. These are especially the compounds of formula I

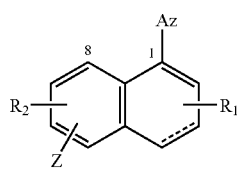

wherein the dotted line denotes an additional bond or no additional bond, Az is imidazolyl, triazolyl or tetrazolyl bonded via a ring nitrogen atom, each of those radicals being unsubstituted or substituted at carbon atoms by lower alkyl or by aryl-lower alkyl, Z is carboxy, lower alkoxycarbonyl, carbamoyl, N-lower alkylcarbamoyl, N,N-di-lower alkylcarbamoyl, N-arylcarbamoyl, cyano, halogen, hydroxy, lower alkoxy, aryl-lower alkoxy, aryloxy, lower alkyl, trifluoromethyl or aryl-lower alkyl, and $R_1$ and $R_2$, independently of one another, are each hydrogen, lower alkyl, lower alkoxy, hydroxy, halogen or trifluoromethyl; aryl being phenyl or naphthyl each of which is unsubstituted or substituted by one or two substituents from the group consisting of lower alkyl, lower alkoxy, hydroxy, halogen and trifluoromethyl; with the proviso that neither Z nor $R_2$ is hydroxy in the 8-position, and pharmaceutically acceptable salts thereof.

Individual compounds from that group that may be given special mention are:
(1) 6-cyano-1-(1-imidazolyl-3,4-dihydronaphthalene,
(2) 6-cyano-1-[1-(1,2,4-triazolyl)]-3,4-dihydronaphthalene,
(3) 6-chloro-1-(1-imidazolyl)-3,4-dihydronaphthalene,
(4) 6-bromo-1-(1-imidazolyl)-3,4-dihydronaphthalene.

(f) The compounds of formula I as defined in Swiss Patent Application 3014/90-0. These are especially the compounds of formula I

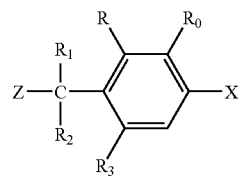

wherein Z is a five-membered nitrogen-containing heteroaromatic ting selected from the group 5-isothiazolyl, 5-thiazolyl, 5-isoxazolyl, 5-oxazolyl, 5-(1,2,3-thiadiazolyl), 5-(1,2,3-oxadiazolyl), 3-(1,2,5-thiadiazolyl), 3-(1,2,5-oxadiazolyl), 4-isothiazolyl, 4-isoxazolyl, 4-(1,2,3-thiadiazolyl), 4-(1,2,3-oxadiazolyl), 2-(1,3,4-thiadiazolyl), 2-(1,3,4-oxadiazolyl), 5-(1,2,4-thiadiazolyl) and 5-(1,2,4-oxadiazolyl); R and $R_0$ are hydrogen; or R and $R_0$ together are a benzo group that is unsubstituted or substituted by lower alkyl, lower alkoxy, hydroxy, halogen or by trifluoromethyl; $R_1$ is hydrogen, hydroxy, chlorine or fluorine; $R_3$ is hydrogen; $R_2$ is hydrogen, lower alkyl or phenyl that is unsubstituted or substituted by lower alkyl, lower alkoxy, hydroxy, halogen, trifluoromethyl or by cyano; or $R_1$ and $R_2$ together are methylidene; or $R_2$ and $R_3$ together are —$(CH_2)_3$—; or $R_1$ and $R_2$ and $R_3$ together are a group =CH—$(CH_2)_2$— wherein the single bone is linked to the benzene ring; X is cyano; and X may also be halogen when $R_2$ and $R_3$ together are —$(CH_2)_3$— or $R_1$ and $R_1$ and $R_3$ together are a group =CH—$(CH_2)_2$—; and pharmaceutically acceptable salts thereof.

Individual compounds from that group that may be given special mention are:
(1) 4-[α-(4-cyanophenyl)-α-hydroxy-5-isothiazolylmethyl]-benzonitrile,
(2) 4-[α-(4-cyanophenyl)-5-isothiazolylmethyl]-benzonitrile,
(3) 4-[α-(4-cyanophenyl)-5-thiazolylmethyl]-benzonitrile,
(4) 1-(4-cyanophenyl)-1-(5-thiazolyl)-ethylene,
(5) 6-cyano-1-(5-isothiazolyl)-3,4-dihydronaphthalene,
(6) 6-cyano-1-(5-thiazolyl)-3,4-dihydronaphthalene.

(g) The compounds of formula VI as defined in Swiss Patent Application 3014/90-0. These are especially the compounds of formula VI

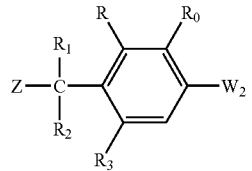

wherein Z is a five-membered nitrogen-containing heteroaromatic ring selected from the group 5-isothiazolyl, 5-thiazolyl, 5-isoxazolyl, 5-oxazolyl, 5-(1,2,3-thiadiazolyl), 5-(1,2,3-oxadiazolyl) 3-(1,2,5-thiadiazolyl), 3-(1,2,5-oxadiazolyl), 4-isothiazolyl, 4-isoxazolyl, 4-(1,2,3-thiadiazolyl), 4-(1,2,3-oxadiazolyl), 2-(1,3,4-thiadiazolyl), 2-(1,3,4-oxadiazolyl), 5-(1,2,4-thiadiazolyl) and 5-(1,2,4-oxadiazolyl); R and $R_0$ are each hydrogen; or R and $R_0$ together are a benzo group that is unsubstituted or substituted by lower alkyl, lower alkoxy, hydroxy, halogen or by trifluoromethyl; $R_1$ is hydrogen, hydroxy, chlorine or fluorine; $R_3$ is hydrogen; $R_2$ is hydrogen, lower alkyl or phenyl that is unsubstituted or substituted by lower alkyl, lower alkoxy, hydroxy, halogen, trifluoromethyl, aryl-lower alkoxy or by aryloxy; or $R_1$ and $R_2$ together are methylidene, and $W_2$ is halogen, hydroxy, lower alkoxy, aryl-lower alkoxy or aryloxy; aryl in each case being phenyl that is unsubstituted or substituted by lower alkyl, lower alkoxy, hydroxy, halogen or by trifluoromethyl; and pharmaceutically acceptable salts thereof.

Individual compounds from that group that may be given special mention are:
(1) bis(4,4'-bromophenyl)-(5-isothiazolyl)methanol,
(2) bis(4,4'-bromophenyl)-(5-isothiazolyl)methane,
(3) bis(4,4'-bromophenyl)-(5-thiazolyl)methanol,
(4) bis(4,4'-bromophenyl)-(5-thiazolyl)methane,
(h) The compounds of formula I as defined in Swiss Patent Application 3923/90-4. These are especially the compounds of formula I

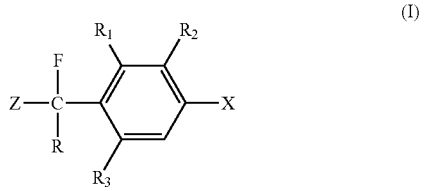

wherein Z is imidazolyl, triazolyl, tetrazolyl, pyrrolyl, pyrazolyl, indolyl, isoindolyl, benzimidazolyl, benzopyrazolyl, benzotriazolyl, pyridyl, pyrimidyl, pyrazinyl, pyridazinyl, triazinyl, quinolinyl or isoquinolinyl, all those radicals being bonded via their heterocyclic rings and all those radicals being unsubstituted or substituted by lower alkyl, hydroxy, lower alkoxy, halogen or by trifluoromethyl: $R_1$ and $R_2$, independently of one another, are each hydrogen or lower alkyl; or $R_1$ and $R_2$ together are $C_3$-$C_4$ alkylene, or a benzo group that is unsubstituted or substituted as indicated below for aryl; R is hydrogen, lower alkyl, aryl or heteroaryl, and X is cyano, carbamoyl, N-lower alkylcarbamoyl, N,N-di-lower alkylcarbamoyl, N,N-lower alkylenecarbamoyl; N,N-lower alkylenecarbamoyl interrupted by —O—, —S— or —NR"—, wherein R" is hydrogen, lower alkyl or lower alkanoyl; N-cycloalkylcarbamoyl, N-(lower alkyl-substituted cycloalkyl)-carbamoyl, N-cycloalkyl-lower alkylcarbamoyl, N-(lower alkyl-substituted cycloalkyl)-lower alkylcarbamoyl, N-aryl-lower alkylcarbamoyl, N-arylcarbamoyl, N-hydroxycarbamoyl, hydroxy, lower alkoxy, aryl-lower alkoxy or aryloxy; and wherein X is also halogen when Z is imidazolyl, triazolyl, tetrazolyl, pyrrolyl, pyrazolyl, indolyl, isoinidolyl, benzimidazolyl, benzopyrazolyl or benzotriazolyl; wherein aryl is phenyl or naphthyl, these radicals being unsubstituted or substituted by from 1 to 4 substituents from the group consisting of lower alkyl, lower alkenyl, lower alkynyl, lower alkylene (linked to two adjacent carbon atoms), $C_3$-$C_8$ cycloalkyl, phenyl-lower alkyl, phenyl; lower alkyl that is substituted in turn by hydroxy, lower alkoxy, phenyl-lower alkoxy, lower alkanoyloxy, halogen, amino, lower alkylamino, di-lower alkylamino, mercapto, lower alkylthio, lower alkylsulfinyl, lower alkylsulfonyl, carboxy, lower alkoxycarbonyl, carbamoyl, N-lower alkylcarbamoyl, N,N-di-lower alkylcarbamoyl and/or by cyano; hydroxy; lower alkoxy, halo-lower alkoxy, phenyl-lower alkoxy, phenoxy, lower alkenyloxy, halo-lower alkenyloxy, lower alkynyloxy, lower alkylenedioxy (linked to two adjacent carbon atoms), lower alkanoyloxy, phenyl-lower alkanoyloxy, phenylcarbonyloxy, mercapto, lower alkylthio, phenyl-lower alkylthio, phenylthio, lower alkylsulfinyl, phenyl-lower alkylsulfinyl, phenylsulfinyl, lower alkylsulfonyl, phenyl-lower alkylsulfonyl, phenylsulfonyl, halogen, nitro, amino, lower alkylamino, $C_3$-$C_8$ cycloalkylamino, phenyl-lower alkylamino, phenylamino, di-lower alkylamino, N-lower alkyl-N-phenylamino, N-lower alkyl-N-phenyl-lower alkylamino; lower alkyleneamino or lower alkyleneamino interrupted by —O—, —S— or —NR"— (wherein R" is hydrogen, lower alkyl or lower alkanoyl); lower alkanoylamino, phenyl-lower alkanoylamino, phenylcarbonylamino, lower alkanoyl, phenyl-lower alkanoyl, phenylcarbonyl, carboxy, lower alkoxycarbonyl, carbamoyl, N-lower alkylcarbamoyl, N,N-di-lower alkylcarbamoyl, N,N-lower alkylenecarbamoyl; N,N-lower alkylenecarbamoyl interrupted by —O—, —S— or —NR"—, wherein R" is hydrogen, lower alkyl or lower alkanoyl; N-cycloalkylcarbamoyl, N-(lower alkyl-substituted cycloalkylycarbamoyl, N-cycloalkyl-lower alkylcarbamoyl, N-(lower alkyl-substituted cycloalkyl)lower alkylcarbamoyl, N-hydroxycarbamoyl, N-phenyl-lower alkylcarbamoyl, N-phenylcarbamoyl, cyano, sulfo, lower alkoxysulfonyl, sulfamoyl, N-lower alkylsulfamoyl, N,N-di-lower alkylsulfamoyl and N-phenylsulfamoyl; the phenyl groups occurring in the substituents of phenyl and naphthyl in turn being unsubstituted or substituted by lower alkyl, lower alkoxy, hydroxy, halogen and/or by trifluoromethyl; wherein heteroaryl is indolyl, isoindolyl, benzimidazolyl, benzopyrazolyl, benzotriazolyl, benzo[b]furanyl, benzo[b]thienyl, benzoxazolyl or benzothiazolyl, those radicals being unsubstituted or substituted by from 1 to 3 identical or different substituents selected from lower alkyl, hydroxy, lower alkoxy, halogen, cyano and trifluoromethyl; and pharmaceutically acceptable salts thereof.

Those compounds are especially the compounds of formula I whereto Z is 1-imidazolyl, 1-(1,2,4-triazolyl), 1-(1,3,4-triazolyl), 1-(1,2,3-triazolyl), 1-tetrazolyl, 2-tetrazolyl, 3-pyridyl, 4-pyridyl, 4-pyrimidyl, 5-pyrimidinyl or 2-pyrazinyl; $R_1$ and $R_2$, independently of one another, are each hydrogen or lower alkyl; or $R_1$ and $R_2$ together are 1,4-butylene or a benzo group; R is lower alkyl; phenyl that is unsubstituted or substituted by cyano, carbamoyl, halogen, lower alkyl, trifluoromethyl, hydroxy, lower alkoxy or by phenoxy; or benzotriazolyl or benzo[b]furanyl, the last two radicals being unsubstituted or substituted by from 1 to 3 identical or different substituents selected from lower alkyl, halogen and cyano; and X is cyano or carbamoyl; and wherein X is also halogen when Z is 1-imidazolyl, 1-(1,2,4-triazolyl), 1-(1,3,4-triazolyl), 1-(1,2,3-triazolyl), 1-tetrazolyl 2-tetrazolyl; and pharmaceutically acceptable salts thereof.

Individual compounds that may be given special mention here are:
(1) 4-[α-4-cyanophenyl)-α-fluoro-1-(1,2,4-triazolyl)methyl]-benzonitrile,
(2) 4-[α-(4-cyanophenyl)-α-fluoro-(2-tetrazolyl)methyl]-benzonitrile,
(3) 4-[α-(4-cyanophenyl)-α-fluoro-(1-tetrazolyl)methyl]-benzonitrile, (4) 4-[α-(4-cyanophenyl)-α-fluoro-(1-imidazolyl)methyl]-benzonitrile,
(5) 1-methyl-6-[α-(4-chlorophenyl)-α-fluoro-1-(1,2,4-triazolyl)methyl]-benzotriazole,
(6) 4-[α-(4-cyanophenyl)-α-fluoro-1-(1,2,3-triazolyl)methyl]-benzonitrile,
(7) 7-cyano-4-[α-(4-cyanophenyl)-α-fluoro-1-(1,2,4-triazolyl)methyl]-2,3-dimethylbenzo[b]furan,
(8) 4-[α-(4-bromophenyl)-α-fluoro-1-(1,2,4-triazolyl)methyl]-benzonitrile,
(9) 4-[α-(4-cyanophenyl)-α-fluoro-(5-pyrimidyl)methyl]-benzonitrile,
(10) 4-[α-(4-bromophenyl)-α-fluoro-(5-pyrimidyl)methyl]-benzonitrile,
(11) 4-[α-(4-cyanophenyl)-α-fluoro-(3-pyridyl)methyl]-benzonitrile,
(12) 7-bromo-4-[α-(4-cyanophenyl)-α-fluoro-(1-imidazolyl)methyl]-2,3-dimethylbenzo[b]furan,
(13) 7-bromo-4-[α-(4-cyanophenyl)-α-fluoro-1-(1,2,4-triazolyl)methyl]-2,3-dimethylbenzo[b]furan,
(14) 4-[α-(4-cyanophenyl)-α-fluoro-(5-pyrimidyl)methyl]-benzonitrile,
(15) 4-[α-(4-bromophenyl)-α-fluoro-(5-pyrimidyl)methyl]-benzonitrile,
(16) 4-[α-(4-cyanophenyl)-1-(1,2,3-triazolyl)methyl]-benzonitrile,
(17) 2,3-dimethyl-4-[α-(4-cyanophenyl)-1-(1,2,4-triazolyl)methyl]-7-cyano-benzo[b]furan,
(18) 4-[α-(4-cyanophenyl)-(5-pyrimidyl)methyl]-benzonitrile,
(19) 4-[α-(4-bromophenyl)-(5-pyrimidyl)methyl]-benzonitrile,
(20) 2,3-dimethyl-4-[α-(4-cyanophenyl)-(1-imidazolyl)methyl]-7-bromo-benzo[b]furan,
(21) 2,3-dimethyl-4-[α-(4-cyanophenyl)-1-(1,2,4-triazolyl)methyl]-7-bromo-benzo-[b]furan.

(i) The compounds of formula I as defined in EP-A-114 033. These are especially the compounds of formula I

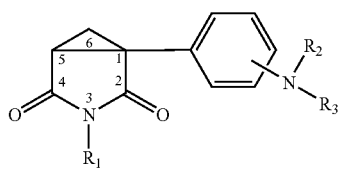

wherein $R_1$ is hydrogen, $R_2$ is hydrogen, sulfo, $C_1$-$C_7$ alkanoyl or $C_1$-$C_7$ alkanesulfonyl and $R_3$ is hydrogen, or wherein $R_1$ is $C_1$-$C_{12}$ alkyl, $C_2$-$C_{12}$ alkenyl, $C_2$-$C_7$ alkynyl, $C_3$-$C_{10}$ cycloalkyl, $C_3$-$C_{10}$ cycloalkenyl, $C_3$-$C_6$ cycloalkyl-$C_1$-$C_4$ alkyl, $C_3$-$C_6$ cycloalkyl-$C_2$-$C_4$ alkenyl or $C_3$-$C_6$ cycloalkenyl-$C_1$-$C_4$ alkyl, $R_2$ is hydrogen, $C_1$-$C_7$ alkyl, sulfo, $C_1$-$C_7$ alkanoyl or $C_1$-$C_7$ alkanesulfonyl and $R_3$ is hydrogen or $C_1$-$C_7$ alkyl, and salts of those compounds.

Individual compounds from that group that may be given special mention are:
(1) 1-(4-aminophenyl)-3-methyl-3-azabicyclo[3.1.0]hexane-2,4-dione,
(2) 1-(4-aminophenyl)-3-n-propyl-3-azabicyclo[3.1.0]hexane-2,4-dione,
(3) 1-(4-aminophenyl)-3-isobutyl-3-azabicyclo[3.1.0]hexane-2,4-dione,
(4) 1-(4-aminophenyl)-3-n-heptyl-3-azabicyclo[3.1.0]hexane-2,4-dione,
(5) 1-(4-aminophenyl)-3-cyclohexylmethyl-3-azabicyclo[3.1.0]hexane-2,4-dione.

(j) The compounds of formula I as defined in EP-A-166 692. These are especially the compounds of formula I

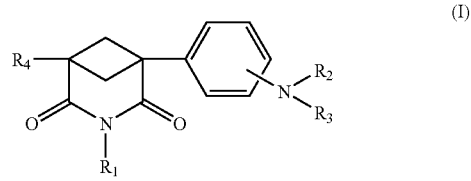

wherein $R_1$ is hydrogen, alkyl having from 1 to 12 carbon atoms, alkenyl having from 2 to 12 carbon atoms, lower alkynyl, cycloalkyl or cycloalkenyl each having from 3 to 10 carbon atoms, cycloalkyl-lower alkyl having from 4 to 10 carbon atoms, cycloalkyl-lower alkenyl having from 5 to 10 carbon atoms, cycloalkenyl-lower alkyl having from 4 to 10 carbon atoms, or aryl having from 6 to 12 carbon atoms or aryl-lower alkyl having from 7 to 15 carbon atoms, each of which is unsubstituted or substituted by lower alkyl, hydroxy, lower alkoxy, acyloxy, amino, lower alkylamino, di-lower alkylamino, acylamino amino or by halogen, $R_2$ is hydrogen, lower alkyl, sulfo, lower alkanoyl or lower alkanesulfonyl, sulfonyl, $R_3$ is hydrogen or lower alkyl and $R_4$ is hydrogen, lower alkyl, phenyl or phenyl substituted by —N($R_2$)($R_3$), and salts thereof, radicals described as "lower" containing up to and including 7 carbon atoms.

Individual compounds from that group that may be given special mention are:
(1) 1-(4-aminophenyl)-3-n-propyl-3-azabicyclo[3.1.1]heptane-2,4-dione,
(2) 1-(4-aminophenyl)-3-methyl-3-azabicyclo[3.1.1]heptane-2,4-dione,
(3) 1-(4-aminophenyl)-3-n-decyl-3-azabicyclo[3.1.1]heptane-2,4-dione,
(4) 1-(4-aminophenyl)-3-cyclohexyl-3-azabicyclo[3.1.1]heptane-2,4-dione,
(5) 1-(4-aminophenyl)-3-cyclohexylmethyl-3-azabicyclo[3.1.1]heptane-2,4-dione.

(k) The compounds of formula I as defined in EP-A-356 673. These are especially the compounds of formula I

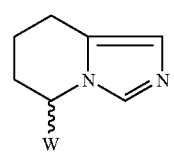

wherein W(α) is a 2-naphthyl or 1-anthryl radical, wherein each benzene ring is unsubstituted or substituted by a substituent selected from halogen, hydroxy, carboxy, cyano and nitro; or (.beta.) is 4-pyridyl, 2-pyrimidyl or 2-pyrazinyl, each of those radicals being unsubstituted or substituted by a substituent selected from halogen, cyano, nitro, $C_1$-$C_4$ alkoxy and $C_2$-$C_5$ alkoxycarbonyl; and pharmaceutically acceptable salts thereof.

Individual compounds from that group that may be given special mention are:
(1) 5-(2'-naphthyl)-5,6,7,8-tetrahydroimidazo[1,5-a]pyridine,
(2) 5-(4'-pyridyl)-5,6,7,8-tetrahydroimidazo[1,5-a]pyridine.
(l) The compounds of formula I or Ia as defined in EP-A-337 929. These are especially the compounds of formula I/Ia

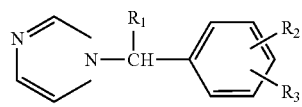

(I/Ia)

wherein $R_1$ is hydrogen, methyl, ethyl, propyl, propenyl, isopropyl, butyl, hexyl, octyl, decyl, cyclopentyl, cyclohexyl, cyclopentylmethyl, cyclohexylmethyl or benzyl, $R_2$ is benzyloxy, 3-bromo-, 4-bromo-, 4-chloro-, 2,3-, 2,4-, 4,5- or 4,6-dichloro-benzyloxy, and $R_3$ is cyano; $C_2$-$C_{10}$ alkanoyl that is unsubstituted or mono- or poly-substituted by halogen, methoxy, amino, hydroxy and/or by cyano; benzoyl that is unsubstituted or substituted by one or more substituents from the group halogen, $C_1$-$C_4$ alkyl, methoxy, amino, hydroxy and cyano; carboxy, (methoxy, ethoxy or butoxy)-carbonyl, carbamoyl, N-isopropylcarbamoyl, N-phenylcarbamoyl, N-pyrrolidylcarbonyl, nitro or amino; and salts thereof.

Individual compounds from that group that may be given special mention are:
(1) 4-(2,4-dichlorobenzyloxy)-3-[1-(1-imidazolyl)-butyl]-benzonitrile,
(2) (4-(4-bromobenzyloxy)-3-[1-(1-imidazolyl)-butyl]-phenyl pentyl ketone,
(3) 4-(4-bromobenzyloxy)-3-[1-(1-imidazolyl)-butyl]-benzanilide,
(4) 4-(4-bromobenzyloxy)-3-[1-(1-imidazolyl)-butyl]-benzoic acid,
(5) 3-(2,4-dichlorobenzyloxy)-4-[1-(1-imidazolyl)-butyl]-benzonitrile,
(6) 3-(2,4-dichlorobenzyloxy)-4-[1-(1-imidazolyl)-butyl]-benzoic acid methyl ester,
(7) 3-(2,4-dichlorobenzyloxy)-4-[1-(1-imidazolyl)-butyl]-benzoic acid,
(8) 3-(3-bromobenzyloxy)-4-[1-(1-imidazolyl)-butyl]-benzonitrile,
(9) 4-(3-bromobenzyloxy)-3-[1-(1-imidazolyl)-butyl]-benzonitrile,
(10) 3-(4-bromobenzyloxy)-4-[1-(1-imidazolyl)-butyl]-benzoic acid,
(11) 3-(4-bromobenzyloxy)-4-[1-(1-imidazolyl)-butyl]-benzanilide,
(12) 3-(4-bromobenzyloxy)-4-[1-(1-imidazolyl)-butyl]-phenyl pentyl ketone,
(13) 4-(4-bromobenzyloxy)-3-[1-(1-imidazolyl)-butyl]-benzonitrile,
(14) 3-(4-bromobenzyloxy)-4-[1-(1-imidazolyl)-butyl]-benzonitrile,
(15) 4-nitro-2-[1-(1-imidazolyl)-butyl]-phenyl-(2,4-dichlorobenzyl) ether,
(16) 4-amino-2-[1-(1-imidazolyl)-butyl]-phenyl-(2,4-dichlorobenzyl) ether,
(17) (2,4-dichlorobenzyl)-[2-(1-imidazolyl-methyl)-4-nitrophenyl]ether.

(m) The compounds of formula I as defined in EP-A-337 928. These are especially the compounds of formula I

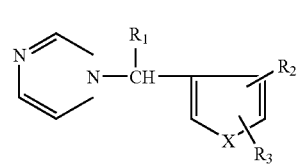

(I)

wherein $R_1$ is hydrogen, methyl, ethyl, propyl, propenyl, isopropyl, butyl, hexyl, octyl, decyl, cyclopentyl, cyclohexyl, cyclopentylmethyl, cyclohexylmethyl or benzyl, $R_2$ is hydrogen, halogen, cyano, methyl, hydroxymethyl, cyanomethyl, methoxymethyl, pyrrolidinylmethyl, carboxy, (methoxy, ethoxy or butoxy)-carbonyl, carbamoyl, N-isopropylcarbamoyl, N-phenylcarbamoyl, N-pyrrolidylcarbonyl; $C_2$-$C_{10}$ alkanoyl that is unsubstituted or mono- or poly-substituted by halogen, methoxy, ethoxy, amino, hydroxy and/or by cyano; or benzoyl that is unsubstituted or substituted by one or more substituents from the group halogen, $C_1$-$C_4$ alkyl, methoxy, ethoxy, amino, hydroxy and cyano, $R_3$ is hydrogen, benzyloxy, 3-bromo, 4-bromo-, 4-chloro-, 2,3-, 2,4-, 4,5- or 4,6-dichlorobenzyloxy, and X is —CH=N—; —CH=N(—O)— or —S—; and salts thereof.

Individual compounds from that group that may be given special mention are:
(1) 5-[1-(1-imidazolyl)-butyl]-thiophene-2-carbonitrile,
(2) 2-[1-(1-imidazolyl)-butyl]-thiophene-4-carbonitrile,
(3) 2-[1-(1-imidazolyl)-butyl]-4-bromo-thiophene,
(4) 2-[1-(1-imidazolyl)-butyl]-5-bromo-thiophene,
(5) 5-[1-(1-imidazolyl)-butyl]-2-thienyl pentyl ketone,
(6) 5-[1-(1-imidazolyl)-butyl]-2-thienyl ethyl ketone,
(7) 5-(4-chlorobenzyloxy)-4-[1-(1-imidazolyl)-pentyl]-pyridine-2-carbonitrile,
(8) 3-(4-chlorobenzyloxy)-4-[1-(1-imidazolyl)-pentyl]-pyridine-2-carbonitrile,
(9) 3-(4-chlorobenzyloxy)-4-[1-(1-imidazolyl)-pentyl]-pyridine-N-oxide,
(10) 3-(4-chlorobenzyloxy)-4-[1-(1-imidazolyl)-pentyl]-pyridine.

(n) The compounds of formula I as defined in EP-A-340 153. These are especially the compounds of formula I

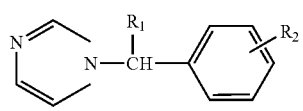

(I)

wherein $R_1$ is hydrogen, methyl, ethyl, propyl, propenyl, isopropyl, butyl, hexyl, octyl, decyl, cyclopentyl, cyclohexyl, cyclopentylmethyl, cyclohexylmethyl or benzyl, and $R_2$ is a radical from the group methyl, ethyl, propyl, benzyl, phenyl and ethenyl that is substituted by hydroxy, cyano, methoxy, butoxy, phenoxy, amino, pyrrolidinyl, carboxy, lower alkoxycarbonyl or by carbamoyl; or $R_2$ is formyl or derivatised formyl that can be obtained by reaction of the formyl group with an amine or amine derivative from the group hydroxylamine, O-methylhydroxylamine, O-ethylhydroxylamine, O-allylhydroxylamine, O-benzylhydroxylamine, O-4-nitrobenzyloxyhydroxylamine, O-2,3,4,5,6-pentafluorobenzyloxyhydroxylamine, semicarbazide, thiosemicarbazide, ethylamine and aniline; acetyl, propionyl, butyryl, valeryl, caproyl; benzoyl that is unsubstituted or substituted by one or more substituents from the group halogen, $C_1$-$C_4$-alkyl, methoxy, amino, hydroxy and cyano; carboxy, (methoxy, ethoxy or butoxy)carbonyl, carbamoyl, N-isopropylcarbamoyl, N-phenylcarbamoyl or N-pyrrolidylcarbonyl; and salts thereof.

Individual compounds from that group that may be given special mention are:
(1) 4-(1-(1-imidazolyl)-butyl)-benzoic acid methyl ester,
(2) 4-(1-(1-imidazolyl)-butyl)-benzoic acid butyl ester,
(3) 4-(1-(1-imidazolyl)-butyl)-phenyl-acetonitrile,
(4) 4-(1-(1-imidazolyl)-butyl)-benzaldehyde,
(5) 4-(1-(1-imidazolyl)-butyl)-benzyl alcohol,
(6) {4-[1-(1-imidazolyl)-butyl]-phenyl}-2-propyl ketone,
(7) 4-[1-(1-imidazolyl)-butyl]-phenyl propyl ketone,
(8) 4-[1-(1-imidazolyl)-butyl]-phenyl butyl ketone,
(9) 4-[1-(1-imidazolyl)-butyl]-phenyl pentyl ketone,
(10) 4-[1-(1-imidazolyl)-butyl]-phenyl hexyl ketone.

(o) The compounds of formula I as defined in DE-A4 014 006. These are especially the compounds of formnula I

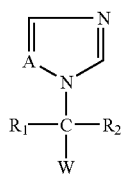

wherein A is an N-atom or a CH radical and W is a radical of the formula

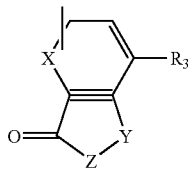

wherein X is an oxygen or a sulfur atom or a —CH=CH— group and Y is a methylene group, an oxygen or a sulfur atom and Z is a —(CH$_2$)$_n$— group wherein n=1, 2 or 3 and either
a) $R_3$ in W is a hydrogen atom and $R_1$ and $R_2$, independently of one another, are each a hydrogen atom, a $C_1$— to $C_{10}$ alkyl group or a $C_3$— to $C_7$ cycloalkyl group, or
b) $R_2$ is as defined under a) and $R_1$ together with $R_3$ forms a —(CH$_2$)$_m$— group wherein m=2, 3, or 4, and their pharmaceutically acceptable addition salts with acids.

Individual compounds from that group that may be given special mention are:
(1) 5-[1-(1-imidazolyl)-butyl]-1-indanone,
(2) 7-[1-(1-imidazolyl)-butyl]-1-indanone,
(3) 6-[1-(1-imidazolyl)butyl]-1-indanone,
(4) 6-(1-imidazolyl)-6,7,8,9-tetrahydro-1H-benz[e]inden-3 (2H)-one,
(5) 2-[1-(1-imidazolyl)-butyl]-4,5-dihydro-6-oxo-cyclopenta[b]-thiophene,
(6) 6-[1-(1-imidazolyl)-butyl]-3,4-dihydro-2H-naphthalen-1-one,
(7) 2-[1-(1-imidazolyl)-butyl]-6,7-dihydro-5H-benzo[b]thiophen-4-one,
(8) 6-[1-(1-imidazolyl)-butyl]-2H-benzo[b]furan-3-one,
(9) 5-[cyclohexyl-(1-imidazolyl)-methyl]-1-indanone,
(10) 2-[1-(1-imidazolyl)butyl]-4,5-dihydro-6H-benzo[b]thiophen-7-one,
(11) 5-[1-(1-imidazolyl)-1-propyl-butyl]-1-indanone,
(12) 2-[1-(1-imidazolyl)-butyl]-4,5-dihydro-6H-benzo[b]thiophen-7-one,
(13) 2-[1-(1-imidazolyl)-butyl]-4,5-dihydro-6-oxo-cyclopenta[b]-thiophene,
(14) 5-(1-imidazolylmethyl)-1-indanone,
(15) 5-[1-(1,2,4-triazolyt)-methyl]-1-indanone.

(p) The compounds of formula I as disclosed in DE-A-3 926 365. These are especially the compounds of formula I

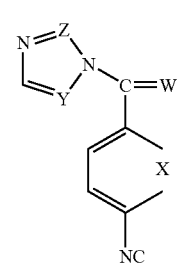

wherein W' is a cyclopentylidene, cyclohexylidene, cycloheptylidene or 2-adamantylidene radical, X is the grouping —CH=CH—, an oxygen or a sulfur atom, and Y and Z, independently of one another, are each a methine group (CH) or a nitrogen atom, and their pharmaceutically acceptable addition salts with acids.

Individual compounds from that group that may be given special mention are:
(1) 4-[1-cyclohexylidene-1-(imidazolyl)-methyl]-benzonitrile,
(2) 4-[1-cyclopentylidene-1-(imidazolyl)-methyl]-benzonitrile,
(3) 4-[1-cycloheptylidene-1-(imidazolyl)-methyl]-benzonitrile,
(4) 4-[2-adamantylidene-1-(imidazolyl)-methyl]-benzonitrile,
(5) 4-[1-cyclohexylidene-1-(1,2,4-triazolyl)-methyl]-benzonitrile,
(6) 4-[1-cyclopentylidene-1-(1,2,4-triazolyl)-methyl]-benzonitrile,
(7) 4-[1-cycloheptylidene-1-(1,2,4-triazolyl)-methyl]-benzonitrile,
(8) 4-[2-adamantylidene-1-(1,2,4-triazolyl)-methyl]-benzonitrile,
(9) 4-[1-cyclohexylidene-1-(1,2,3-triazolyl)-methyl]-benzonitrile,
(10) 4-[1-cyclopentylidene-1-(1,2,3-triazolyl)-methyl]-benzonitrile,
(11) 5-[cyclohexylidene-1-imidazolylmethyl]-thiophene-2-carbonitrile.

(q) The compounds of formula I as defined in DE-A-3 740 125. These are especially the compounds of formula I

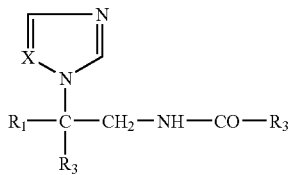

(I)

wherein X is CH or N, $R_1$ and $R_2$ are identical or different and are each phenyl or halophenyl, and $R_3$ is $C_1$-$C_4$ alkyl; $C_1$-$C_4$ alkyl substituted by CN, $C_1$-$C_4$ alkoxy, benzyloxy or by $C_1$-$C_4$ alkoxy-(mono-, di- or tri-)ethyleneoxy; $C_1$-$C_4$ alkoxy, phenyl; phenyl that is substituted by halogen or by cyano; a $C_5$-$C_7$ cycloalkyl group that is optionally condensed by benzene, or is thienyl, pyridyl or 2- or 3-indolyl; and acid addition salts thereof.

An individual compound from that group that may be given special mention is:
(1) 2,2-bis(4-chlorophenyl)-2-(1H-imidazol-1-yl)-1-(4-chlorobenzoyl-amino) ethane.

(r) The compounds of formula I as defined in EP-A-293 978. These are especially the compounds of formula I

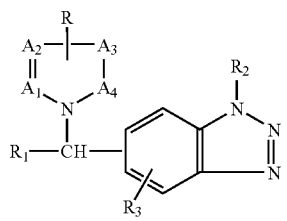

(I)

pharmaceutically acceptable salts and stereochemically isomeric forms thereof, wherein $-A_1=A_2-A_3=A_4-$ is a divalent radical selected from —CH=N—CH=CH—, —CH=N—CH=N— and —CH=N—N=CH—, R is hydrogen or $C_1$-$C_6$ alkyl; $R_1$ is hydrogen, $C_1$-$C_{10}$ alkyl, $C_3$-$C_7$ cycloalkyl, $Ar_1$, $Ar_2$-$C_1$-$C_6$ alkyl, $C_2$-$C_6$ alkenyl or $C_2$-$C_6$ alkynyl: $R_2$ is hydrogen; $C_1$-$C_{10}$ alkyl that is unsubstituted or substituted by $Ar_1$; $C_3$-$C_7$ cycloalkyl, hydroxy, $C_1$-$C_6$ alkoxy, $Ar_1$, $C_2$-$C_6$ alkenyl, $C_2$-$C_6$ alkynyl, $C_3$-$C_7$ cycloalkyl, bicyclo[2.2.1]heptan-2-yl, 2,3-dihydro-1H-indenyl, 1,2,3,4-tetrahydronaphthyl, hydroxy; $C_2$-$C_6$ alkenyloxy that is unsubstituted or substituted by $Ar_2$; $C_2$-$C_6$ alkynyloxy; pyrimidyloxy; di($Ar_2$) methoxy, (1-$C_1$-$C_4$ alkyl-4-piperidinyl)oxy, $C_1$-$C_{10}$ alkoxy; or $C_1$-$C_{10}$ alkoxy that is substituted by halogen, hydroxy, $C_1$-$C_6$ alkyloxy, amino, mono- or di-($C_1$-$C_6$ alkyl)amino, trifluoromethyl, carboxy, $C_1$-$C_6$ alkoxycarbonyl, Ar.sub.I, $Ar_2$-O—, $Ar_2$-S—, $C_3$-$C_7$ cycloalkyl, 2,3-dihydro-1,4-benzodioxinyl, 1H-benzimidazolyl, $C_1$-$C_4$ alkyl-substituted 1H-benzimidazolyl, (1,1'-biphenyl)-4-yl or by 2,3-dihydro-2-oxo-1H-benzimidazolyl; and $R_3$ is hydrogen, nitro, amino, mono- or di-($C_1$-$C_6$ alkyl)amino, halogen, $C_1$-$C_6$ alkyl, hydroxy or $C_1$-$C_6$ alkoxy; wherein $Ar_1$ is phenyl, substituted phenyl, naphthyl, pyridyl, aminopyridyl, imidazolyl, triazolyl, thienyl, halothienyl, furanyl, $C_1$-$C_6$ alkylfuranyl, halofuranyl or thiazolyl; wherein $Ar_2$ is phenyl, substituted phenyl or pyridyl; and wherein "substituted phenyl" is phenyl that is substituted by up to 3 substituents in each case selected independently of one another from the group consisting of halogen, hydroxy, hydroxymethyl, trifluoromethyl, $C_1$-$C_6$ alkyl, $C_1$-$C_6$ alkoxy, $C_1$-$C_6$ alkoxycarbonyl, carboxy, formyl, hydroxyiminomethyl, cyano, amino, mono- and di-($C_1$-$C_6$ alkyl)amino and nitro.

Individual compounds from that group that may be given special mention are:
(1) 6-[(1H-imidazol-1-yl)-phenylmethyl]-1-methyl-1H-benzotriazole,
(2) 6-[(4-chlorophenyl)(1H-1,2,4-triazol-1-yl)methyl]-1-methyl-1H-benzotriazole.

(s) The compounds of formula II as defined in EP-A-250 198, especially
(1) 2-(4-chlorophenyl)-1,1-di(1,2,4-triazol-1-ylmethyl)ethanol,
(2) 2-(4-fluorophenyl)-1,1-di(1,2,4-triazol-1-ylmethyl)ethanol,
(3) 2-(2-fluoro-4-trifluoromethylphenyl)-1,1-di(1,2,4-triazol-1-ylmethyl)ethanol,
(4) 2-(2,4-dichlorophenyl)-1,1-di(1,2,4-triazol-1-ylmethyl) ethanol,
(5) 2-(4-chlorophenyl)-1,1-di(1,2,4-triazol-1-ylmethyl)-ethanol,
(6) 2-(4-fluorophenyl)-1,1-di(1,2,4-triazol-1-yl-methyl) ethanol.

(t) The compounds of formula I as defined in EP-A-281 283, especially
(1) (1R*2R*)-6-fluoro-2-(4-fluorophenyl)-1,2,3,4-tetrahydro-1-(1H-1,2,4-triazol-1-yl-methyl)naphthalene,
(2) (1R*,2R* )-6-fluoro-2-(4-fluorophenyl)-1,2,3,4-tetrahydro-1-(1H-imidazolylmethyl)-naphthalene,
(3) (1R*,2R*)- and (1R*,2S*)-2-(4-fluorophenyl)-1,2,3,4-tetrahydro-1-(1H-1,2,4-triazol-1-ylmethyl)naphthalene-6-carbonitrile,
(4) (1R*,2R*)- and (1R*,2S*)-2-(4-fluorophenyl)-1,2,3,4-tetrahydro-1-(1H-imidazolylmethyl)naphthalene-6-carbonitrile,
(5) (1R*,2R*)- and (1R*,2S*)-1,2,3,4-tetrahydro-1-(1H-1,2,4-triazol-1-ylmethyl)-naphthalene-2,6-dicarbonitrile,
(6) (1R*,2R*)- and (1R*,2S*)-1,2,3,4-tetrahydro-1-(1H-imidazol-1-ylmethyl)naphthalene-2,6-dicarbonitrile,
(7) (1R*,2S*)-2-(4-fluorophenyl)-1,2,3,4-tetrahydro-1-(5-methyl-1H-imidazolyl-methyl)naphthalene-6-carbonitrile.

(u) The compounds of formula I as defined in EP-A-296 749, especially
(1) 2,2'-[5-(1H-1,2,4-triazol-1-ylmethyl)-1,3-phenylene]di(2-methylpropiononitrile),
(2) 2,2'-[5-(imidazol-1-ylmethyl)-1,3-phenylene]di(2 methylpropiononitrile),
(3) 2-[3-(1-hydroxy-1-methylethyl)-5-(5H-1,2,4-triazol-1-ylmethyl)phenyl]-2-methylpropiononitrile,
(4) 2,2'-[5-dideuterio(1H-1,2,4-triazol-1-yl)methyl-1,3-phenylene]di(2-trideuteriomethyl-3,3,3-trideuteriopropiononitrile),
(5) 2,2'-[5-dideuterio(1H-1,2,4-triazol-1-yl)methyl-3-phenylene]di(2methylpropiononitrile).

(v) The compounds of formula I as defined in EP-A-299 683, especially
(1) (Z)-α-(1,2,4-triazol-1-ylmethyl)stilbene-4,4'-dicarbonitrile,
(2) (Z)-4'-chloro-α-(1,2,4-triazol-1-ylmethyl)stilbene-4-carbonitrile,
(3) (Z)-α-(1,2,4-triazol-1-ylmethyl)-4'-(trifluoromethyl)stilbene-4-carbonitrile,
(4) (E)-.beta.-fluoro-α-(1,2,4-triazol-1-ylmethyl)stilbene-4,4'-dicarbonitrile, (5) (Z)-4'-fluoro-α-(imidazol-1-ylmethyl)stilbene-4-carbonitrile,
(6) (Z)-2',4'-dichloro-α-(imidazol-1-ylmethyl)stilbene-4-carbonitrile,
(7) (Z)-4'-chloro-α-(imidazol-1-ylmethyl)stilbene-4-carbonitrile,
(8) (Z)-α-(imidazol-1-ylmethyl)stilbene-4,4'dicarbonitrile,
(9) (Z)-α-(5-methylimidazol-1-ylmethyl)stilbene-4,4'-dicarbonitrile,
(10) (Z)-2-[2-(4-cyanophenyl)-3-(1,2,4-triazol-1-yl)propenyl]pyridine-5-carbonitrile.
(w) The compounds of formula I as defined in EP-A-299 684, especially
(1) 2-(4-chlorobenzyl)-2-fluoro-1,3-di(1,2,4-triazol-1-yl)propane,
(2) 2-fluoro-2-(2-fluoro4-chlorobenzyl)-1,3-di(1,2,4-triazol-1-yl)propane,
(3) 2-fluoro-2-(2-fluoro-4-trifluoromethylbenzyl)-1,3-di(1,2,4-triazol-1-yl)propane,
(4) 3-(4-chlorophenyl)-1-(1,2,4-triazol-1-yl )-2-(1,2,4-triazol-1-ylmethyl)butan-2-ol,
(5) 2-(4-chloro-α-fluorobenzyl)-1,3-di(1,2,4-triazol-1-yl)propan-2-ol,
(6) 2-(4-chlorobenzyl)-1,3-bis(1,2,4-triazol-1-yl)propane,
(7) 4-[2-(4-chlorophenyl)-1,3-di(1,2,4-triazol-1-ylmethyl)ethoxymethyl]-benzonitrile,
(8) 1-(4-fluorobenzyl)-2-(2fluoro-4-trifluoromethylphenyl)-1,3-di(1,2,4-triazol-1-yl)-propan-2-ol,
(9) 2-(4-chlorophenyl)-1-(4-fluorophenoxy)-1,3-di(1,2,4-triazol-1-yl)propan-2-ol,
(10) 1-(4-cyanobenzyl)-2-(2,4-difluorophenyl)-1,3di(1,2,4-triazol-1-yl)propan-2-ol,
(11) 2-(4-chlorophenyl)-1-phenyl-1,3-di(1,2,4-triazol-1-yl)propan-2-ol.
(x) The compounds as defined in claim 1 of EP-A-316 097, especially
(1) 1,1-dimethyl-8-(1H-1,2,4-triazol-1-ylmethyl)-2(1H)-naphtho[2,1-b]furanone,
(2) 1,2-dihydro1,1-dimethyl-2-oxo-8-(1H-1,2,4-triazol-1-ylmethyl)naphtho[2,1-b]-furan-7-carbonitrile,
(3) 1,2-dihydro-1,1-dimethyl-2-oxo-8-(1H-1,2,4-triazol-1-ylmethyl)naphtho[2,1-b]-furan-7-carboxamide,
(4) 1,2-dihydro-1,1-dimethyl-2-oxo-8-[di(1H-1,2,4-triazol-1-yl)methyl]naphtho[2,1-b]-furan-7-carbonitrile.
(y) The compounds of formula I as defined in EP-A-354 689, especially
(1) 4-[2-(4-cyanophenyl)-3-(1,2,4-triazol-1-yl)propyl]benzonitrile,
(2) 4-[1-(4-chlorobenzyl)-2-(1,2,4-triazol-1-yl)ethyl]benzonitrile,
(3) 4-[2-(1,2,4-triazol-1-yl)-1-(4-trifluoromethyl]benzyl)ethyl]benzonitrile,
(4) 4-[2-(1,2,4-triazol-1-yl)-1-(4-[trifluoromethoxy]benzyl)ethyl]benzonitrile.
(z) The compounds of formula (1) as defined in EP-A-354 683, especially
(1) 6-[2-(4-cyanophenyl)-3-(1,2,4-triazol-1-yl)-propyl]nicotinonitrile,
(2) 4-[1-(1,2,4-triazol-1-yl-methyl)-2-(5-[trifluoromethyl]pyrid-2-yl)ethyl]benzonitrile.

Examples of steroidal aromatase inhibitors that may be mentioned are:
(aa) The compounds of formula I as defined in EP-A-181 287. These are especially the compounds of formula I

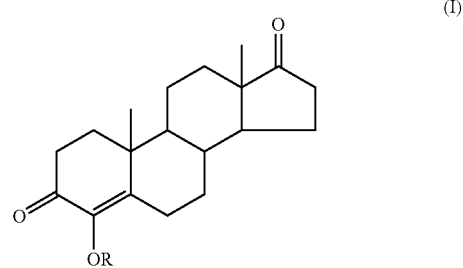

wherein R is hydrogen, acetyl, heptanoyl or benzoyl. An individual compound from that group that may be given special mention is:
(1) 4-hydroxy-4-androstene-3,17-dione.
(ab) The compounds as defined in the claims of U.S. Pat. No. 4,322,416, especially 10-(2-propynyl)-oestr-4-ene-3,17-dione.
(ac) The compounds as defined in the claims of DE-A-3 622 841, especially 6-methyleneandrosta-1,4-diene-3,17-dione.
(ad) The compounds as defined in the claims of GB-A-2 17 1100, especially 4-amino-androsta-1,4,6-triene-3,17-dione.
Also: (ae) androsta-1,4,6-triene-3,17-dione.

The content of the patent applications mentioned under (a) to (z) and (aa) to (ad), especially the subgroups of compounds disclosed therein and the individual compounds disclosed therein as examples, have been incorporated by reference into the disclosure of the present application.

The general terms used hereinbefore and hereinafter to define the compounds have the following meanings:

Organic radicals designated by the term "lower" contain up to and including 7, preferably up to and including 4, carbon atoms.

Acyl is especially lower alkanoyl.

Aryl is, for example, phenyl or 1- or 2-naphthyl, each of which is unsubsttuted or substituted by lower alkyl, hydroxy, lower alkoxy, lower alkanoyloxy, amino, lower alkylamino, di-lower alkylamino, lower alkanoylamino or by halogen.

Pharmaceutically acceptable salts of the above-mentioned compounds are, for example, pharmaceutically acceptable acid addition salts or pharmaceutically acceptable metal or ammonium salts.

Pharmaceutically acceptable acid addition salts are especially those with suitable inorganic or organic acids, for example strong mineral acids, such as hydrochloric acid, sulfuric acid or phosphoric acid, or organic acids, especially aliphatic or aromatic carboxylic or sulfonic acids, for example formic, acetic, propionic, succinic, glycolic, lactic, hydroxysuccinic, tartaric, citric, maleic, fumaric, hydroxymaleic, pyruvic, phenylacetic, benzoic, 4-aminobenzoic, anthranilic, 4-hydroxybenzoic, salicylic, 4-aminosalicylic, pamoic, gluconic, nicotinic, methanesulfonic, ethanesulfonic, halobenzenesulfonic, p-toluenesulfonic, naphthalenesulfonic, sulfanilic or cyclohexylsulfamic acid; or with other acidic organic substances, for example ascorbic acid. Pharmaceutically acceptable salts may also be formed, for example, with amino acids, such as arginine or lysine.

Compounds containing acid groups, for example a free carboxy or sulfo group, can also form pharmaceutically acceptable metal or ammonium salts, such as alkali metal or alkaline earth metal salts, for example sodium, potassium, magnesium or calcium salts, also ammonium salts derived from ammonia or suitable organic amines. Them come into consideration especially aliphatic, cycloaliphatic, cycloaliphatic-aliphatic or araliphatic primary, secondary or tertiary mono-, di- or poly-amines, such as lower alkylamines, for example di- or tri-ethylamine, hydroxy-lower alkylamines, for example 2-hydroxyethylamine, bis(2-hydroxyethyl)amine or tris(2-hydroxyethyl)amine, basic aliphatic esters or carboxylic acids, for example 4-aminobenzoic acid 2-diethylaminoethyl ester, lower alkyleneamines, for example 1-ethylpiperidine, cycloalkylamines, for example dicyciohexyiamine, benzylamines, for example N,N'-dibenzylethylenediamine; also heterocyclic bases, for example of the pyridine type, for example pyridine, collidine or quinoline. If several acidic or basic groups are present, mono- or poly-salts can be formed. Compounds according to the invention having an acidic and a basic group may also be in the form of internal salts, i.e. in the form of zwitterions and another part of the molecule in the form of a normal salt.

In the case of the above-mentioned individual compounds the pharmaceutically acceptable salts are included in each case insofar as the individual compound is capable of salt formation.

The compounds listed, including the individual compounds mentioned, both in free form and in salt form, may also be in the form of hydrates, or their crystals may include, for example, the solvent used for crystallisation. The present invention relates also to all those forms.

Many of the above-mentioned compounds, including the individual compounds mentioned, contain at least one asymmetric carbon atom. They can therefore occur in the form of R— or S-enantiomers and as enantiomeric mixtures thereof, for example in the form of a racemate. The present invention relates to the use of all those forms and to the use of all further isomers, and of mixtures of at least 2 isomers, for example mixtures of diastereoisomers or enantiomers which can occur when there are one or more further asymmetric centres in the molecule. Also included are, for example, all geometric isomers, for example cis- and trans-isomers, that can occur when the compounds contain one or more double bonds.

The daily doses required for the present invention depend entirely on the type of aromatase inhibitor that is used. Some inhibitors are more active than others and hence lower amounts of the former inhibitors could be used. The particular patient also determines dosage levels.

Typically, the amount of aromatase inhibitor may be selected from amounts that lower estrogen levels to postmenopausal levels in a female. For example the amount of aromatase inhibitor may be selected from amounts that lower the level of estrogen to about 100 pmol/L or less as measured by standard immunoassay techniques. These techniques are well known to those skilled in the art.

Examples of preferred suitable dosages are as follows. When the aromatase inhibitor is letrozole, it is preferably administered in a daily dose of from about 2.5 mg to about 5.0 mg. When the aromatase inhibitor is anastrozole, preferably, it is administered in a daily dose of from about 1 mg to about 2 mg. When the aromatase inhibitor is vorozole, the preferred daily dose is from about 2 to about 4 mg. Exemestane is preferably administered in a daily dose of about 25 mg.

Preferred is a total of 2 to 10 daily doses of the aromatase inhibitor with administration starting on any of days 1 to 5 of the menstrual cycle, where the female is ovulating. Most preferably the daily doses of the aromatase inhibitor comprise five daily doses.

The FSH used may be any of the commercially available products, the majority of which are produced by recombinant means. FSH may also be used in a form, which includes LH (Luteinizing Hormone).

The dosages for FSH may range from about 25 to about 600 units daily or its equivalent in other delivery forms with the period of administration being from about 1 to about 15 days. The FSH may be administered simultaneously, consecutively, with or without a gap or with some dosage overlap.

Other types of ovulatory infertility which may be treated in accordance with the present invention may include endometriosis, cervical mucus abnormalities, older patients, increased baseline FSH concentration, elevated FSH concentration, and low male sperm count requiring IUI (Intrauterine Insemination) or TDI (therapeutic donor insemination) in which augmenting ovulation in the female partner is indicated.

Pharmaceutical Formulations

The pharmaceutical compositions that can be prepared according to the invention are compositions for enteral, such as peroral or rectal administration, also for transdermal or sublingual administration, and for parenteral, for example intravenous, subcutaneous and intramuscular, administration. Suitable unit dose forms, especially for peroral and/or sublingual administration, for example dragees, tablets or capsules, comprise preferably from approximately 0.01 mg to approximately 20 mg, especially from approximately 0.1 mg to approximately 10 mg, of one of the above-mentioned compounds or of a pharmaceutically acceptable salt thereof, together with pharmaceutically acceptable carriers. The preferred form of administration is oral. The proportion of active ingredient in such pharmaceutical compositions is generally from approximately 0.001% to approximately 60%, preferably from approximately 0.1% to approximately 20%.

Suitable excipients for pharmaceutical compositions for oral administration are especially fillers, such as sugars, for example lactose, saccharose, mannitol or sorbitol, cellulose preparations and/or calcium phosphates, for example tricalcium phosphate or calcium hydrogen phosphate, and binders, such as starches, for example corn, wheat, rice or potato starch, gelatin, tragacanth, methylcellulose and/or hydroxypropylcellulose, disintegrators, such as the above-mentioned starches, also carboxymethyl starch, cross-linked polyvinylpyrrolidone, agar, alginic acid or a salt thereof, such as sodium alginate, and/or cellulose, for example in the form of crystals, especially in the form of microcrystals, and/or flow regulators and lubricants, for example silicic acid, talc, stearic acid or salts thereof, such as magnesium or calcium stearate, cellulose and/or polyethylene glycol.

Dragee cores can be provided with suitable, optionally enteric, coatings, there being used inter alia concentrated sugar solutions which may comprise gum arabic, talc, polyvinylpyrrolidone, polyethylene glycol and/or titanium dioxide, or coating solutions in suitable solvents or solvent mixtures, or, for the preparation of enteric coatings, solutions of suitable cellulose preparations, such as acetylcellulose phthalate or hydroxypropylmethylcellulose phthalate.

Other orally administrable pharmaceutical compositions are dry-filled capsules consisting of gelatin, and also soft sealed capsules consisting of gelatin and a plasticiser, such as glycerol or sorbitol. The dry-filled capsules may contain the active ingredient in the form of granules, for example in admixture with fillers, such as lactose, binders, such as starches, and/or glidants, such as talc or magnesium stearate, and, if desired, stabilisers. In soft capsules, the active ingredient is preferably dissolved or suspended in suitable oily excipients, such as fatty oils, paraffin oil or liquid polyethylene glycols, to which stabilisers and/or anti-bacterial agents may also be added. There may also be used capsules that are easily bitten through, in order to achieve by means of the sublingual ingestion of the active ingredient that takes place as rapid an action as possible.

Suitable rectally or transvaginally administrable pharmaceutical compositions are, for example, suppositories that consist of a combination of the active ingredient with a suppository base. Suitable suppository bases are, for example, natural or synthetic triglycerides, paraffin hydrocarbons, polyethylene glycols or higher alkanols. There may also be used gelatin rectal capsules, which contain a combination of the active ingredient with a base material. Suitable base materials are, for example, liquid triglycerides, polyethylene glycols or paraffin hydrocarbons.

Suitable formulations for transdermal administration comprise the active ingredient together with a carrier. Advantageous carriers include absorbable pharmacologically acceptable solvents that serve to facilitate the passage through the skin of the host. Transdermal systems are usually in the form of a bandage that comprises a support, a supply container containing the active ingredient, if necessary together with carriers, optionally a separating device that releases the active ingredient onto the skin of the host at a controlled and established rate over a relatively long period of time, and means for securing the system to the skin.

Suitable for parenteral administration are especially aqueous solutions of an active ingredient in water-soluble form, for example in the form of a water-soluble salt, and also suspensions of active ingredient, such as corresponding oily injection suspensions, there being used suitable lipophilic solvents or vehicles, such as fatty oils, for example sesame oil, or synthetic fatty acid esters, for example ethyl oleate, or triglycerides, or aqueous injection suspensions that comprise viscosity-increasing substances, for example sodium carboxymethylcellulose, sorbitol and/or dextran, and, optionally, stabilisers.

Dyes or pigments may be added to the pharmaceutical compositions, especially to the tablets or dragee coatings, for example for identification purposes or to indicate different doses of active ingredient.

The pharmaceutical compositions of the present invention can be prepared in a manner known per se, for example by means of conventional mixing, granulating, confectioning, dissolving or lyophilising processes. For example, pharmaceutical compositions for oral administration can be obtained by combining the active ingredient with solid carriers, optionally granulating a resulting mixture, and processing the mixture or granules, if desired or necessary after the addition of suitable excipients, to form tablets or dragee cores.

EXAMPLES

The invention that is claimed is described in detail in the following Examples, which are intended merely to illustrate the invention, and in no way to represent a limitation thereof.

Example 1

In this example the use of the AI, letrozole, for ovulation induction in 10 patients who either failed to ovulate (n=3) or ovulated with an endometrial thickness <5 mm (n=7) in response to CC administration was examined. In all patients, letrozole treatment was given orally, at least two months after the last CC cycle, in a dose of 2.5 to 5 mg/day, from days 3 to 7 or 5 to 9 of the menstrual cycle. HCG 10,000 IU was given to all except one patient to trigger ovulation. Ten patients completed 12 cycles (one patient completed three cycles). Ovulation occurred in 9 cycles (75%) and pregnancy in 4 out of 10 patients (40%). The data is presented in Table 1 below.

TABLE 1

|  | Age | Day of HCG admin. | Follicles >1.5 Cm On day of HCG admin. | Endometrial Thickness (Cm.) | Estradiol on day of HCG admin. (pmol) | LH on day of HCG admin. (IU/L) |
| --- | --- | --- | --- | --- | --- | --- |
| Mean | 33.4 | 15 | 2 | 0.8 | 1036 | 16 |
| Range | 28-40 | 11-18 | 1-3 | 0.6-0.9 | 107-2347 | 3.1-66 |
| Median | 33.5 | 15 | 2 | 0.8 | 988 | 7.8 |

From the above-mentioned data, the use of letrozole for obtaining multiple follicles in ovulation induction protocols appears to be effective.

Example 2

Eight patients with unexplained infertility undergoing intrauterine insemination (IUI) received hFSH (human FSH) from cycle day 3 and were considered poor responders (<3 dominant follicles) during 16 FSH-only cycles. Subsequently, they were offered letrozole 2.5 mg/day from days 3 to 7 of the menstrual cycle with FSH (50-225 IU/day) starting on day 7. HCG (10,000 IU) was given when leading follicles were >2 cm followed by IUI. The mean+SD age and duration of infertility were 36.5+2.96 and 4.6+1.2 years, respectively. The data appears in Table 2 below.

TABLE 2

|  | FSH only (16 cycles) | Letrozole + FSH (8 cycles) | P value |
| --- | --- | --- | --- |
| FSH/cycle (IU) | 1469 + 498 | 603 + 510 | <0.05 |
| Stimulation days/cycle | 9.1 + 3 | 6.8 + 2.4 | NS |
| Day of HCG administration | 12.2 + 2.9 | 13.3 + 2.1 | NS |
| Number of mature follicles | 1.88 + 0.7 | 3.5 + 1.3 | <0.05 |
| E2 on HCG day (pmol/L) | 1893 + 1066 | 1689 + 1044 | NS |
| E2/mature follicle on HCG day (pmol/L) | 1097 + 557 | 483 + 259 | <0.05 |
| Endometrial thickness on HCG day (cm) | 0.92 + 0.15 | 0.93 + 0.14 | NS |
| LH on HCG day (IU/L) | 14.7 + 13.2 | 10.4 + 8.5 | NS |

NS = Not significant

During letrozole+FSH cycles two pregnancies were achieved (25%). In this example, a potential benefit of letrozole for improving ovarian response to FSH in poor responders is shown. The dose of FSH was significantly reduced as compared with administration of FSH alone and the number of mature follicles was significantly increased.

Example 3

Fifteen patients who either failed to ovulate (6 cycles) or ovulated with an endometrial thickness <5 mm (24 cycles) in response to CC and who did not conceive were given letrozole orally, at least two months after the last CC cycle, in a dose of 2.5 to 5 mg/day, from day 3 to 7 or 5 to 9 of the menstrual cycle. HCG 10,000 IU was given to trigger ovulation. CC was given in a dose of 50-100 mg on days 3-7 or 5-9.

Fifteen patients completed 17 letrozole cycles. Ovulation occurred in 13 cycles (77%) and pregnancy in 5 out of 15 patients (33%). The following table shows summary of CC and letrozole cycles.

TABLE 3

| Treatment | Mean Letrozole | Mean CC | P | Range Letrozole | Range CC | Median Letrozole | Median CC |
|---|---|---|---|---|---|---|---|
| Day of hCG administration | 14.5 | 12.6 | S | 11-18 | 11-16 | 15 | 12 |
| Number of Days from last letrozole tablet to HCG day | 6.7 | 4.4 | S | 2-9 | 2-7 | 7 | 4 |
| Endometrial Thickness (Cm.) | 0.8 | 0.5 | S | 0.6-1.1 | 0.4-0.8 | 0.8 | 0.4 |
| Follicles >1.5 Cm on day of hCG administration | 2.4 | 1.9 | NS | 1-3 | 1-5 | 2 | 2 |
| Estradiol (pmol/L) on day of hCG administration | 1016 | 2145 | S | 107-2347 | 362-5210 | 901 | 1668 |
| Estradiol per mature follicle (pmol/L) | 392 | 1278 | S | 107-837 | 177-2404 | 289 | 1486 |
| LH on day of hCG administration (IU/L) | 16 | 16 | NS | 3.1-66 | 3-66 | 8.2 | 8 |

P value (<0.005 = significant)
S = Significant
NS = Not Significant

These results illustrate the improvement letrozole offers over CC.

Example 4

This was a controlled study that included prospectively two study groups who received letrozole, 2.5 mg/day from day 3 to 7 of the menstrual cycle, in addition to FSH, and two control groups received FSH only. The study groups included 15 PCOS patients and 12 unexplained infertility patients. The control groups consisted of 25 PCOS patients and 55 unexplained infertility patients. All patients received recombinant or highly purified FSH (50-150 IU/day starting on day 3 to 7 until day of hCG (10,000 IU) that was given when 2 leading follicles were >2 cm). The FSH regimen was based on the patient's clinical profile. Patients were not randomized. All patients had intrauterine insemination. There was no statistically significant difference between the study and control groups as regards age, weight, infertility duration, number of prior insemination cycles, semen parameters or type of FSH.

The FSH needed was statistically significantly lower when letrozole was used in both study groups compared with the control groups. However, there was no significant difference, in number of follicles >1.8 cm., endometrial thickness, LH level or day of HCG administration. Estradiol level was statistically significantly lower in letrozole/FSH cycles but still in the normal physiological range. Pregnancy rate was (20%) in both PCOS study and control groups. In the unexplained infertility groups, pregnancy rate was 25% in the study group versus 18% in the control group. The difference was not significant.

It would seem that inhibition of estrogen synthesis by AI in the early part of the menstrual cycle would release the estrogenic negative feedback resulting in an increase in gonadotropin secretion. Moreover, by inhibiting the conversion of androgens into estrogens, the accumulating androgens may increase follicular sensitivity to FSH through amplification of FSH receptor gene expression. This example demonstrates the result of applying AI to improve the response to FSH without having antiestrogenic effects as seen with clomiphene citrate. Such treatment offers a decrease in the expense of gonadotropin treatment and provides a therapy for low responders who require high FSH doses during ovarian stimulation.

TABLE 4

| Treatment | PCOS letrozole + FSH | PCOS FSH only | P value | unexplained infertility Letrozole + FSH | unexplained infertility FSH only | P value |
|---|---|---|---|---|---|---|
| Pregnancy rate | 20% | 20% | ns | 25% | 18% | ns |
| Total FSH dose/cycle (IU) | 525 | 955 | <0.05 | 585 | 1320 | <0.05 |
| Day of hCG admin. | 12 | 12 | ns | 12 | 12 | ns |
| Endometrial thickness (on HCG day) | 11.8 | 11.7 | ns | 11.5 | 12.1 | ns |
| Follicle (>1.8 cm) on hCG day | 3.7 | 3.6 | ns | 3.4 | 3.2 | ns |

TABLE 4-continued

| Treatment | PCOS letrozole + FSH | PCOS FSH only | P value | unexplained infertility Letrozole + FSH | unexplained infertility FSH only | P value |
|---|---|---|---|---|---|---|
| Estradiol on hCG day (pmol/L) | 2010 | 3480 | 0.05 | 2130 | 3140 | <0.05 |
| Estradiol/mature follicle (pmol/L) | 543 | 967 | 0.05 | 626 | 969 | <0.05 |
| LH on hCG day (IU/L) | 15.3 | 17.8 | ns | 16.3 | 18.3 | ns | ns = not significant

BRIEF DESCRIPTION OF THE DRAWINGS

The accompanying figures are meant to illustrate the present invention and should not be used to limit the invention in any way.

DETAILED DESCRIPTION OF THE DRAWINGS

Figure 1:
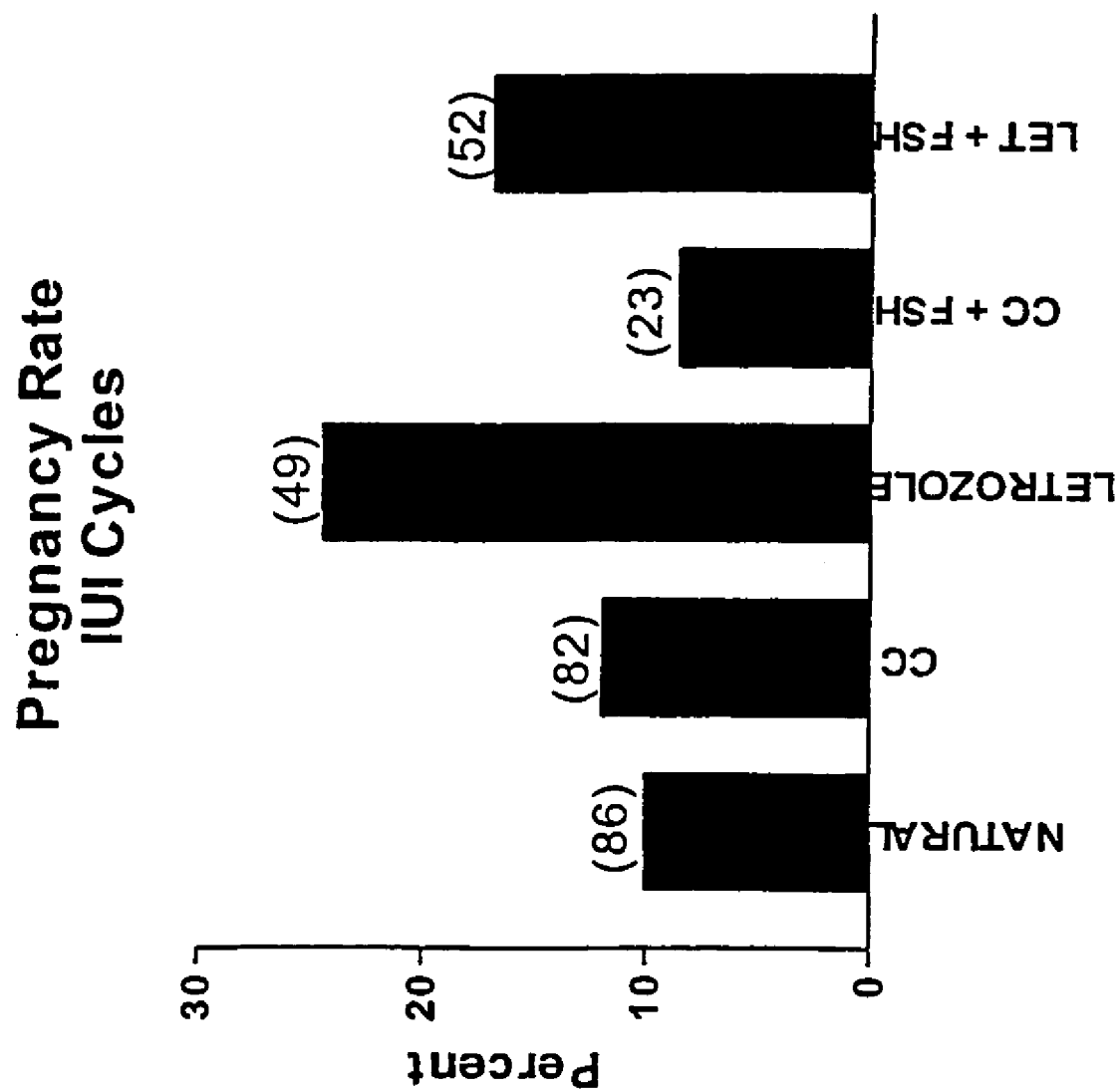
In FIG. 1 there is shown a bar graph of pregnancy rate after intrauterine insemination for patients receiving a variety of fertility treatments including the multiple dose treatments of the present invention.

In FIG. 1, there is shown pregnancy rates for 292 cycles of ovulation induction (PCOS) or ovulation augmentation (unexplained infertility) for intrauterine insemination of washed sperm (IUI) in the Reproductive Biology Unit of the Division of Reproductive Sciences at the University of Toronto during the year 2000. The data was collected retrospectively and the women may have had one or more cycles of each treatment or more than one treatment. Natural refers to no drug treatment in 86 cycles, CC refers to clomiphene citrate (50 to 100 mg per day for 5 days) in 82 cycles, LETROZOLE refers to letrozole (2.5 mg per day for 5 days) in 49 cycles, CC+FSH refers to clomiphene citrate (50 to 100 mg per day for 5 days) plus recombinant follicle stimulating hormone injections (75 to 150 IU per day) until administration of human chorionic gonadotropin (hCG), and LET+FSH refers to letrozole (2.5 mg per day for 5 days) plus recombinant follicle stimulating hormone injections (75 to 150 IU per day) until administration of hCG. Pregnancy was defined as the presence of a gestational sac on ultrasound (clinical pregnancy) and did not include chemical pregnancy (elevated HCG only).

Figure 2:
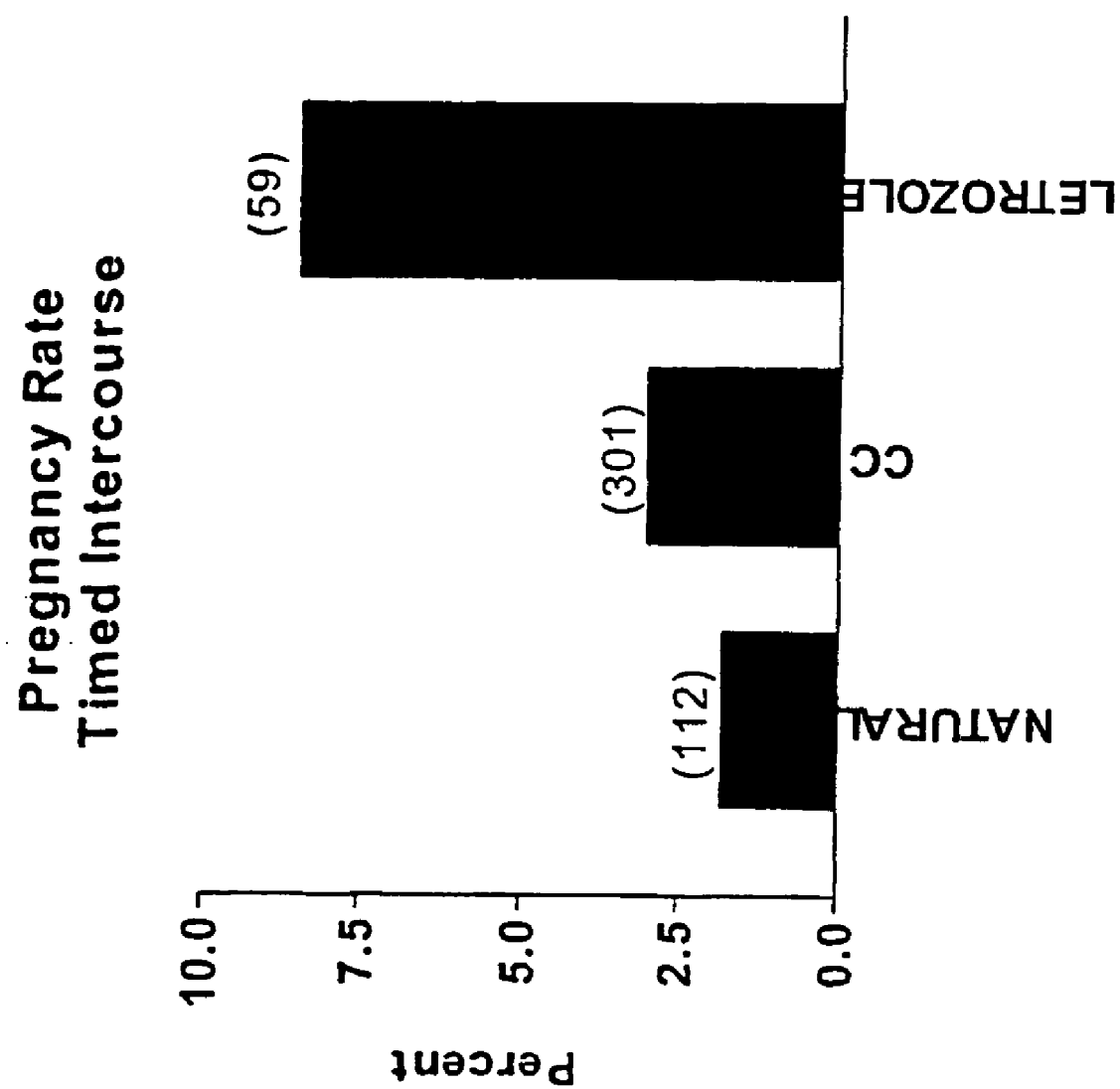
FIG. 2 is a bar graph illustrating pregnancy rate after timed intercourse, the patients having undergone CC and letrozole treatments, with a comparison with a patient group that received no treatment.

In FIG. 2, there is shown pregnancy rates for 472 cycles of ovulation induction (PCOS patients) or ovulation augmentation (unexplained infertility patients) for timed intercourse in the Reproductive Biology Unit of the Division of Reproductive Sciences at the University of Toronto during the year 2000. The data was collected retrospectively and the women may have had one or more cycles of each treatment or more than one treatment. Natural refers to no drug treatment in 112 cycles, CC refers to clomiphene citrate (50 to 100 mg per day for 5 days) in 301 cycles, and LETROZOLE refers to letrozole (2.5 mg per day for 5 days) in 59 cycles. Pregnancy was defined as the presence of a gestational sac on ultrasound (clinical pregnancy) and did not include chemical pregnancy (elevated HCG only).

While the invention has been described with particular reference to certain embodiments thereof, it will be understood that changes and modifications may be made by those of ordinary skill in the art within the scope and spirit of the following claims.

In the claims, the word "comprising" means "including the following elements (in the body), but not excluding others"; the phrase "consisting of" means "excluding more than traces of other than the recited ingredients"; and the phrase "consisting essentially of" means "excluding unspecified ingredients which materially affect the basic characteristics of the composition".

REFERENCES

[1] Garcia J, Jones G S and Wentz A C. The use of clomiphene citrate. Fertil Steril 1977, 28:707-17.

[2] Goldfarb A. F., Morales A., Rakoff A. E. and Protos P. Critical review of 160 clomiphene-related pregnancies. Obstet Gynecol 1968, 31:342-345.

[3] Randall J M, Templeton A. Cervical mucus score and in vitro sperm mucus interaction in spontaneous and clomiphene citrate cycles. Fertil Steril 1991; 56:465-8; and Gelety T J and Buyalos R P. The effect of clomiphene citrate and menopausal gonadotropins on cervical mucus in ovulatory cycles. Fertil Steril 1993, 60:471-476.

[4] Gonen Y, Casper R F. Sonographic Determination of an Adverse Effect of Clomiphene Citrate on Endometrial Growth. Hum Reprod 1990; 5:670-4.

[5] Mikkelson T J, Kroboth P D, Cameron W J, Dittert L W, Chungi V, Manberg P J. Single-dose pharmacokinetics of clomiphene citrate in normal volunteers. Fertil Steril 1986; 46:392-6.

[6] Fluker M R, Unman B, Mackinnon M et al. Exogenous gonadotropin therapy in World Health Organization Groups I and II ovulatory disorders. Obstet Gynecol 1994; 83:189-96.

[7] Fisch P, Casper R F, Brown S E, Wrixon W, Collins J A, Reid R L, Simpson C. Unexplained infertility: evaluation of treatment with clomiphene citrate and human chorionic gonadotropin. Fertil Steril 1989; 51(5): 828-33.

[8] Sereepapong W, Triratanachat S, Sampatanukul P, Pruksananonda K, Boonkasemsanti K and Reinprayoon D. Effects of clomiphene citrate on the endometrium of regularly cycling women. Fertil Steril 2000; (73): 287-91.

[9] Taymor M L. The regulation of follicle growth: some clinical implicatons in reproductive endocrinology. Fertil Steril 1996; 65(2): 235-47

[10] Wysowski D E. Use of fertility drugs in the United States, 1979 through 1991. Fertil Steril 1993;60:1096-98

[11] Adashi: Clomiphene citrate: mechanism(s) and site(s) of action—a hypothesis revisited. Fertil Steril 1984; 42(3): 331-44

[12] Dickey R P, Vorys N, Stevens V C, Besch P K, Hamwi G J, Ullery J C. Observations on the mechanism of action of clomiphene (MRL-41). Fertil Steril 1965;16:485-94

[13] Kettel L M, Roseff S J, Berga S L, Mortola J F, Yen S S. Hypothalamic-pituitary-ovarian response to clomiphene citrate in women with polycystic ovary syndrome. Fertil Steril 1993;59(3):532-8.

[14] Archer D F, Hofmann G. Brzyski R, Ross B, Scott R T, Philput C B, Oehninger S, Ware J C. Effects of clomiphene citrate on episodic luteinizing hormone secretion throughout the menstrual cycle. Am J Obstet Gynecol 1989;161 (3):581-9.

[15] Adashi Clomiphene citrate: mechanism(s) and site(s) of action—a hypothesis revisited. Fertil Steril 1984, 42(3).331-44

[16] Adashi Clomiphene citrate: mechanism(s) and site(s) of action—a hypothesis revisited. Fertil Steril 1984, 42(3): 331-44

[17] Yagel S. Ben-Chetnt A, Anteby E. Zacut D, Hochner-Celnikier D and Ron M. The effect of thinly estradiol on endometnal thickness and uterine volume during ovulation induction by clomiphene citrate. Fertil Steril 1992, 57:33-36.

[18] Ben-Ami M, Geslevich Y, Matilsky M, Battino S, Weiner E et al. Exogenous estrogen therapy concurrent with clomiphene citrate—lack of effect on serum sex hormone levels and endometrial thickness. Gynecol Obstet Invest. 1994; 37(3):180-2.

[19] Bateman B G, Nunley W C Jr and Kolp L A. Exogenous estrogen therapy for treatment of clomiphene citrate-induced cervical mucus abnormalities: is it effective? Fertil Steril 1990, 54:577-9

[20] Wu C H, Winkel C A. The effect of therapy initiation day on clomiphene citrate therapy. Fertil Steril 1989;52:564-568

[21] Saleh A, Biljan M M, Tan SSSL and Tulandi T. Effects of Tamoxifen (Tx) on Endometrial Thickness and Pregnancy Rates in Women Undergoing Superovulation with Clomiphene Citrate (CC) and Intrauterine Insemination (IUI). Fertil Steril 2000; 74(S1):S90

[22] Sioufi A, Gauducheau N, Pineau V, et al: Absolute bioavailability of letrozole in healthy post-menopausal women. Biopharm Drug Dispos 1997; 18:779-89; and Sioufi A, Sandrenan N. Godbillon J, Trunet P, Czendlik C, Howald H, Pfister C, Ezzet F. Comparative bioavailability of letrozole under fed and fasting conditions in 12 healthy subjects after a 2.5 mg single oral administration. Biopharm Drug Dispos 1997; 18(6): 489-97.

[23] Cole P A, Robinson C H. Mechanism and inhibition of cytochrome P-450 aromatase, J. Med. Chem. 33 (1990) 2933-2944; and Akhtar M, Njar V C O, Wright J N. Mechanistic studies on aromatase and related C—C bond cleaving P-450 enzymes, J Steroid Biochem Mol Biol 1993; (44): 375-387.

[24] Santen R J, Manni A, Harvey H, Redmond C. Endocrine treatment of breast cancer in women. Endocrine Rev 1990; 11:1-45.

[25] Nebert D W, Nelson D R, Coon M J, Estabrook R W, Feyereisen R. et al. The P-450 superfamily: update on new sequences, gene mapping and recommended nomenclature, DNA Mol. Biol. 10 (1991) 1-14.

[26] R. C. Coombes, P. Goss, M. Dowsett, J. C. Gazet, A. M. H. Brodie, 4-Hydroxyandrostenedione treatment of post-menopausal patients with advanced breast cancer, The Lancet 2,1984,1237-1239.

[27] Santen R J, Lipton A, Kendall J. Successful medical adrenalectomy with aminoglutethimide: role of altered drug metabolism. J Am Med Assoc 1974;230:1661.

[28] Harris A L, Dowsett M, Smith I E et al. Aminoglutethimide in car-premenopausal patients with breast cancer: endocrine studies and tumour response. Cancer Chemother Pharmacol 1980;5:23.

[29] Marty M, Gershanovich M, Campos B, Romien G, Lurie H, Bonaventura T, et al. AIs, a new potent, selective aromatase inhibitor superior to aminoglutethimide (AG) in postmenopausal women with advanced breast cancer previously treated with antioestrogens. Proc Am Soc Clim Oncol 1997;16:156; and Dowsett M. Biological background to aromatase inhibition. The Breast 1996; 5:196-201.

[30] Sinha S, Kaseta J, Santner L M et al: Effects of CGS20267 on ovarian aromatase and gonadotropin levels in the rat. Breast Cancer Res Treat 1998; 48:45-51.

[31] Shetty G, Krishnamurthy H, Krishnamurthy H N et al: Effect of estrogen deprivation on the reproductive physiology of male and female primates. J Steroid Biochem Biol 1997; 61:157-66.

[32] Geisler J, King N, Dowsett M et al. Influence of anastrozole (Arimidex), a selective, non-steroidal aromatase inhibitor, on in vivo aromatisation and plasma oestrogen levels in postmenopausal women with breast cancer. Br J Cancer 1996; 74: 1286-91.

[33] Sioufi A, Gauducheau N, Pineau V, et al: Absolute bioavailability of letrozole in healthy post-menopausal women. Biopharm Drug Dispos 1997; 18:779-89.

[34] Trunet P F, Mueller P, Bhatnagar P S, Dickes I, Monnet G and White G. Open dose-finding study of a new potent and selective nonsteroidal aromatase inhibitor, CGS 20 267, in healthy male subjects. J Clinc Endocrinol Metab 1993; 77: 319-323.

[35] Femara professional information brochure. Novartis Pharmaceuticals Corporation. East Hanover, N.J. 2000.

[36] Mitwally M F M and Casper R F. The Use of an Aromatase Inhibitor for Induction of Ovulation in Cases of Clomiphene Citrate Failure. [Abstract number O-178] In: Program and abstracts of The 16$^{th}$ Annual Meeting of the European Society for Human Reproduction and Embryology (ESHRE), June 2000, Bologna, Italy; and Mitwally M F M and Casper R F. Aromatase Inhibition: A novel Method of Ovulation Induction in Women With Polycystic Ovarian Syndrome Reprod Technol 2000; 10(5) In Press.

[37] Mitwally M F M and Casper R F. The Aromatase Inhibitor, Letrozole: a Promising Alternative for Clomiphene Citrate for Induction of Ovulation. [Abstract number O-091] In: Program and abstracts of The 56$^{th}$ Annual Meeting of the American Society for Reproductive Medicine (ASRM), October 2000, San Diego, Calif., USA. Winner of the Prize paper award of the Society of Reproductive Endocrinology and Infertility; and Mitwally M F M and Casper R F: Use of an aromatase inhibitor for induction of ovulation in patients with an inadequate response to clomiphene citrate. Fertil Steril 2001; 75(2): 305-9.

[38] Mitwally M F M and Casper R F. The Aromatase Inhibitor, Letrozole, Decreases FSH Dose Required for Ovarian Superovulation. The 46th Annual Meeting of the Canadian Fertility and Andrology Society. Newfoundland, Canada. September 2000; and Mitwally M F M and Casper R F. Aromatase inhibition decreases FSH dose needed during controlled ovarian hyperstimulation: A controlled prospective trial. Meeting of the Society for Gynecologic Investigation, March 2001, Toronto, Canada. Winner of the President Presenter's Award

[39] Mitwally M F M and Casper R F. Aromatase Inhibition Improves Ovarian Response to FSH: A Potential Option for Low Responders During Ovarian Stimulation. The 48th meeting of the Pacific Coast Fertility Society Meeting, Rancho Las Palmas Resort and Spa, Calif., USA. April 2001.

[40] Weil S; Vendola K; Zhou J; Bondy C A. Androgen and follicle-stimulating hormone interactions in primate ovarian follicle development. J Clin Endocrinol Metab 1999; 84(8):2951-6.

[41] Vendola K A, Zhou J, Adesanya O O, Weil S J, Bondy C A. Androgens stimulate early stages of follicular growth in the primate ovary. J Clin Invest 1998;101 (12):2622-9.

The invention claimed is:

1. A method of inducing ovulation in a female suffering from anovulatory infertility which comprises administering to said female at least one 1,2,4-triazole aromatase inhibitor in a dosage amount of from about 0.01 mg/kg/day to about 10 mg/kg/day.

2. The method of claim 1, wherein said at least one 1,2,4-triazole aromatase inhibitor is administered for a period of 4 days.

3. A method of inducing ovulation in a female suffering from anovulatory infertility which comprises administering to said female a 1,2,4-triazole aromatase inhibitor at a daily dose of from about 0.01 mg/day to about 20 mg/day for 2 to 10 consecutive days in a menstrual cycle.

4. The method of claim 3, wherein said 1,2,4-triazole aromatase inhibitor is administered once a day starting on any one of days 1 to 5 of the menstrual cycle.

5. The method of claim 3, wherein said 1,2,4-triazole aromatase inhibitor is administered for 5 consecutive days in a menstrual cycle.

6. The method of claim 5, wherein said 1,2,4-triazole aromatase inhibitor is administered on each of days 3 to 7 of the menstrual cycle.

7. The method of claim 5, wherein said 1,2,4-triazole aromatase inhibitor is administered on each of days 5 to 9 of the menstrual cycle.

8. The method of claim 3, wherein said 1,2,4-triazole aromatase inhibitor is administered at a daily dose of from about 0.1 mg per day to about 10 mg per clay.

9. The method of claim 3, wherein said 1,2,4-triazole aromatase inhibitor is administered at a daily dose of about 2.5 mg/day to about 5 mg/day.

10. The method of claim 3, wherein the 1,2,4-triazole aromatase inhibitor is
(a) letrozole administered in a daily dose of from about 2.5 mg to about 5.0 mg,
(b) anastrozole administered in a daily dose of from about 1 mg to about 2 mg, or
(c) vorozole administered in a daily dose of from about 2 mg to about 4 mg.

11. A method for augmenting ovulation in an ovulating female suffering from infertility which comprises administering to said female two or more daily doses of at least one 1,2,4-triazole aromatase inhibitor on days 1-5 in one or more menstrual cycles.

12. A method of (a) substantially reducing dosage levels of follicle stimulating hormone (FSH) for administration to a female undergoing infertility treatment or (b) increasing response to FSH, which method comprises administering a combination of at least one 1,2,4-triazole aromatase inhibitor (AI) administered on two or more consecutive days in a menstrual cycle with a plurality of doses of follicle stimulating hormone (FSH) administered on two or more consecutive days in the same menstrual cycle.

13. A method of treating infertility in a female comprising administering to said female a 1,2,4-triazole aromatase inhibitor on two or more separate, consecutive days in a menstrual cycle in an amount effective to induce or augment ovulation.

14. The method of claim 13, wherein the daily dose of said 1,2,4-triazole aromatase inhibitor is from about 0.01 mg/day to about 20 mg/day.

15. The method of claim 13, wherein the 1,2,4-triazole aromatase inhibitor is
(a) letrozole administered in a daily dose of from about 2.5 mg to about 5.0 mg,
(b) anastrozole administered in a daily dose of from about 1 mg to about 2 mg, or
(c) vorozole administered in a daily dose of from about 2 mg to about 4 mg.

16. The method of claim 13, wherein the method further comprises administering a plurality of daily doses of follicle stimulating hormone, wherein administration of said 1,2,4-triazole aromatase inhibitor reduces the amount of follicle stimulating hormone required for the treatment of infertility as compared to the amount of follicle stimulating hormone required in the absence of said aromatase inhibitor.

17. The method of claim 16, wherein follicle production in said female is increased in said female as compared to follicle production in the absence of administration of said 1,2,4-triazole aromatase inhibitor.

18. The method of claim 16, wherein the dose of follicle stimulating hormone ranges from about 25 units/day to about 600 units/day or an equivalent dosage in another form of administration.

19. The method of claim 18, wherein the 1,2,4-triazole aromatase inhibitor is (a) letrozole administered at a dose of from about 2.5 mg/day to about 5.0 mg/day, (b) anastrozole administered at a dose of from about 1 mg/day to about 2 mg/day, or (c) vorozole administered at a dose of from about 2 mg/day to about 4 mg/day.

20. The method of claim 13, wherein the amount of 1,2,4-triazole aromatase inhibitor is selected from amounts that lower estrogen levels to post-menopausal levels in a female.

21. The method of claim 20, wherein the amount of 1,2,4-triazole aromatase inhibitor is selected from amounts that lower estrogen levels to about 100 pmol/L or less.

22. The method of claim 13, wherein the 1,2,4-triazole aromatase inhibitor is administered on from 2 to 10 consecutive days starting on any of days 1 to 5 of the menstrual cycle.

* * * * *